(12) United States Patent
Zare et al.

(10) Patent No.: US 6,866,785 B2
(45) Date of Patent: Mar. 15, 2005

(54) PHOTOPOLYMERIZED SOL-GEL COLUMN AND ASSOCIATED METHODS

(75) Inventors: Richard N. Zare, Stanford, CA (US); Maria T. Dulay, Sunnyvale, CA (US); Joselito P. Quirino, Stanford, CA (US); Bryson Bennett, Murray, UT (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 09/929,275

(22) Filed: Aug. 13, 2001

(65) Prior Publication Data

US 2003/0062308 A1 Apr. 3, 2003

(51) Int. Cl.[7] .............................................. B01D 15/08
(52) U.S. Cl. .................... 210/656; 210/635; 210/198.2; 210/658; 210/198.3
(58) Field of Search ................................ 210/635, 656, 210/659, 198.2, 658, 198.3; 95/82, 88; 96/101

(56) References Cited

U.S. PATENT DOCUMENTS

| | | | |
|---|---|---|---|
| 3,503,712 A | 3/1970 | Sussman | 210/198.2 |
| 3,568,840 A | 3/1971 | Hashimoto et al. | 210/198.2 |
| 3,757,490 A | 9/1973 | Ma | 210/198.2 |
| 3,808,125 A | 4/1974 | Good | 210/198.2 |
| 3,878,092 A | 4/1975 | Fuller | 210/198.2 |
| 4,293,415 A | 10/1981 | Bente, III et al. | 210/198.2 |
| 4,323,439 A | 4/1982 | O'Farrell | 204/180 G |
| 4,617,102 A | 10/1986 | Tomblin et al. | 204/299 R |
| 4,675,300 A | 6/1987 | Zare et al. | 436/172 |
| 4,790,919 A | 12/1988 | Baylor, Jr. | 204/182.8 |
| 5,085,756 A | 2/1992 | Swedberg | 204/299 R |
| 5,116,471 A | 5/1992 | Chien et al. | 204/180.1 |
| 5,116,495 A | 5/1992 | Prohaska | 210/198.2 |
| 5,135,627 A | 8/1992 | Soane | 210/198.2 |
| 5,200,150 A * | 4/1993 | Rose, Jr. | 422/62 |
| 5,202,010 A | 4/1993 | Guzman | 204/299 R |
| 5,308,495 A | 5/1994 | Avnir et al. | 210/198.2 |
| 5,316,680 A | 5/1994 | Frechet et al. | 210/198.2 |
| 5,334,310 A | 8/1994 | Frechet et al. | 210/198.2 |
| 5,340,452 A | 8/1994 | Brenner et al. | 204/180.1 |
| 5,423,966 A | 6/1995 | Wiktorowicz | 204/182.8 |
| 5,453,185 A | 9/1995 | Frechet et al. | 210/198.2 |
| 5,453,382 A | 9/1995 | Novotny et al. | 436/178 |
| 5,522,994 A | 6/1996 | Frechet et al. | 210/198.2 |
| 5,599,445 A | 2/1997 | Betz et al. | 210/198.2 |
| 5,624,875 A * | 4/1997 | Nakanishi | 501/39 |

(List continued on next page.)

FOREIGN PATENT DOCUMENTS

| | | | |
|---|---|---|---|
| EP | 0 439 318 A2 | 7/1991 | 210/198.2 |
| EP | 0 779 512 B1 | 6/1997 | 210/198.2 |
| WO | WO 99/30147 | 6/1999 | 210/198.2 |
| WO | WO 00/49396 | 8/2000 | 210/198.2 |

OTHER PUBLICATIONS

Hawley, The Condensed Chemical Dictionary, Van Nostrand, New York, 1971, p. 558.*

C. Yu et al., "Towards Stationary Phases for Chromatography on a Microchip: Molded Porous Polymer Monoliths Prepared in Capillaries by Photoinitiated In Situ Polymerization as Separation Media for Electrochromatography," *Electrophoresis*, vol. 21, 2000, pp. 120–127.

(List continued on next page.)

*Primary Examiner*—Ernest G. Therkorn
(74) *Attorney, Agent, or Firm*—Parsons Hsue & de Runtz LLP

(57) ABSTRACT

A separation column and a method of making the separation column are provided. The separation column includes a separation channel and fritless separation medium in the channel. The separation medium includes a porous matrix, and the porous matrix includes a metal organic polymer, such as a photopolymer. The separation medium can be used to separate a sample of analytes.

8 Claims, 14 Drawing Sheets

U.S. PATENT DOCUMENTS

| | | | |
|---|---|---|---|
| 5,637,135 A | 6/1997 | Ottenstein et al. | 96/101 |
| 5,647,979 A | 7/1997 | Liao et al. | 210/198.2 |
| 5,667,674 A | 9/1997 | Hanggi et al. | 210/198.2 |
| 5,719,322 A | 2/1998 | Lansbarkis et al. | 210/198.2 |
| 5,728,296 A | 3/1998 | Hjerten et al. | 210/198.2 |
| 5,728,457 A | 3/1998 | Frechet et al. | 210/198.2 |
| 5,759,405 A | 6/1998 | Anderson, Jr. et al. | 210/656 |
| 5,766,435 A | 6/1998 | Liao et al. | 204/451 |
| 5,772,875 A | 6/1998 | Pettersson et al. | 210/198.2 |
| 5,800,692 A | 9/1998 | Naylor et al. | 204/601 |
| 5,858,241 A | 1/1999 | Dittmann et al. | 210/656 |
| 5,916,427 A | 6/1999 | Kirkpatrick | 204/469 |
| 5,938,919 A | 8/1999 | Najafabadi | 210/198.2 |
| 6,136,187 A | 10/2000 | Zare et al. | 210/198.2 |
| 6,210,570 B1 * | 4/2001 | Holloway | 210/198.2 |
| 6,398,962 B1 * | 6/2002 | Cabrera | 210/198.2 |
| 6,531,060 B1 * | 3/2003 | Nakanishi | 210/198.2 |
| 6,562,744 B1 * | 5/2003 | Nakanishi | 210/198.2 |

OTHER PUBLICATIONS

J. Quirino et al., "Sweeping of Analyte Zones in Electrokinetic Chromatography," *Analytical Chemistry*, vol. 71, No. 8, Apr. 15, 1999, pp. 1638–1644.

M. Taylor et al., "Analysis of Corticosteroids in Biofliuids by Capillary Electrochromatography with Gradient Elution," *Analytical Chemistry*, vol. 69, No. 13, Jul. 1, 1997, pp. 2554–2558.

D.A. Stead et al., "Capillary Electrochromatography of Steroids Increased Sensitivity by On–Line Concentration and Comparison with High–Performance Liquid Chromatography," *Journal of Chromatography A*, vol. 798, 1998, pp. 259–267.

Y. Zhang et al., "High–Efficiency On–Line Concentration Technique of Capillary Electrochromatography," *Analytical Chemistry*, vol. 72, No. 22, Nov. 15, 2000, pp. 5744–5747.

T. Tegeler et al., "On–Column Trace Enrichment by Sequential Frontal and Elution Electrochromatography. 1. Application to Carbamate Insecticides," *Analytical Chemistry*, vol. 73, No. 14, Jul. 15, 2001, pp. 3365–3372.

F. E. P. Mikkers et al., "Concentration Distributions in Free Zone Electrophoresis," *Journal of Chromatography*, vol. 169, Feb. 1, 1979, pp. 1–10.

R.–L. Chien et al., "On–Column Sample Concentration Using Field Amplification In CZE," *Analytical Chemistry*, vol. 64, No. 8, Apr. 15, 1992, pp. 489A–496A.

J. Quirino et al., "Exceeding 5000–Fold Concentration of Dilute Analytes in Micellar Electrokinetic Chromatography," *Science*, vol. 282, Oct. 16, 1998, pp. 465–468.

C. Yang et al., "Electrically Driven Microseparation Methods for Pesticides and Metabolites. II: On–line and Off–line Preconcentration of Urea Herbicides in Capillary Electrochromatography," *Electrophoresis*, vol. 20, 1999, pp. 2337–2342.

M. Dulay et al., "Preparation and Characterization of Monolithic Porous Capillary Columns Loaded with Chromatographic Particles," *Analytical Chemistry*, vol. 70, No. 23, Dec. 1, 1998, pp. 5103–5107.

M. Dulay et al., "Photopolymerized Sol–Gel Monoliths for Capillary Electrochromatography," *Analytical Chemistry*, vol. 73, No. 16, Aug. 15, 2001, pp. 3921–3926.

J. Quirino et al., "New Strategy for On–Line Preconcentration in Chromatographic Separations," manuscript, undated.

J. Quirino et al., "On–Line Preconcentration in Capillary Electrochromatography Using a Porous Monolith, Solvent Gradient and Sample Stacking," manuscript, undated.

M. Kato et al, "Photopolymerized Sol–Gel Frits for Packed Columns in Capillary Electrochromatography," *Journal of Chromatography A*, vol. 924, 2001, pp. 187–195.

J.–R. Chen et al., "Macroporous Photopolymer Frits for Capillary Electrochromatography," *Analytical Chemistry*, vol. 72, No. 6, Mar. 15, 2000, pp. 1224–1227.

C. Viklund et al., "Molded Macroporous Poly(Glycidyl Methacrylate–Co–Trimethylolpropane Trimethylacrylate) Materials with Fine Controlled Porous Properties: Preparation of Monoliths Using Photoinitiated Polymerization," *Chem. Mater.*, vol. 9, No. 2, 1997, pp. 463–471.

M. Dulay et al., "Bonded–Phase Photopolymerized Sol–Gel Monoliths for Reversed Phase Capillary Electrochromatography," *J. Sep. Sci.*, vol. 25, 2002, pp. 3–9.

M. Kato et al., "Effect of Preparatory Conditions on the Performance of Photopolymerized Sol–Gel Monoliths for Capillary Electrochromatography," *Journal of Chromatography A*, vol. 961, 2002, pp. 45–51.

M. Kato et al., "Enantiomeric Separation of Amino Acids and Nonprotein Amino Acids Using a Particle–Loaded Monolithic Column," *Electrophoresis*, vol. 21, 2000, pp. 3145–3151.

J. Quirino et al., "On–Line Preconcentration in Capillary Electrochromatography Using a Porous Monolith Together with Solvent Gradient and Sample Stacking," *Anal. Chem.*, vol. 73, 2001, pp. 5557–5563.

J. Quirino et al., "Strategy for On–Line Preconcentration in Chromatographic Separations," *Anal. Chem.*, vol. 73, 2001, pp. 5539–5543.

K. Morishima et al., "Toward Sol–Gel Electrochromatographic Separations on a Chip," *J. Sep. Sci.*, vol. 25, 2002, pp. 1226–1230.

M.J. Hilhorst et al., "Sensitivity Enhancement in Capillary Eletrochromatography by On–Column Preconcentration," *Chromatographia 2001*, 53, Feb. (No. ¾), pp. 190–196.

Woo, et al., "Photopolymerization of Methyl Methacrylate with Primary Aryl– and Alkylsilanes," *Bulletin of the Korean Chemical Society*, vol. 16, No. 11, ISSN 0253–2964, Nov. 20, 1995.

Cialko, et al., "Capillary Electrochromatography," *Analyst*, Jul. 1998, vol. 123 pp. 87R–102R.

Quirino, et al., "Sample Stacking of Cationic and Anionic Analytes in Capillary Electrophoresis," *Journal of Chromatography*, A, 902 2000, pp. 119–135.

Quirino, et al., "Sweeping of Neutral Analytes in Electrokinetic Chromatography with HIgh–Salt–Containing Matrixes," *Analytical Chemistry*, vol. 72, No. 8, Apr. 15, 2000.

Chen, et al., "Semipreparative Capillary Electrochromatography." *Analytical Chemistry*, vol. 73, No. 9, May 1, 2001.

Colon, et al., "Packing Columns for Capillary Electrochromatography," *Journal of Chromatography*, A. 887 (2000) pp. 45–53.

Svec, et al., "Design of the Monolithic Polymers used in Capillary Electrochromatography Columns," *Journal of Chromatography*, A, 887 (2000) pp. 3–29.

Constantin, et al., "Preparation of Stationary Phasese for Open–Tubular Capillary Electrochromatography Using the Sol–Gel Method," *Journal of Chromatography*, A, 887 (2000) pp. 253–263.

Tan, et al., "Preparation and Evaluation of Bonded Linear Polymethacrylate Stationary Phases for Open Tubular Capillary Electrokinetic Chromatography," *Analytical Chemistry,* vol. 69, No. 4, Feb. 15, 1997.

Chirica, et al., "Fritless Capillary Columns for HPLC and CEC Prepared by Immobilizing the Stationary Phase in an Organic Polymer Matrix," *Analytical Chemistry,* vol. 72, No. 15, Aug. 1, 2000, pp. 3605–3610.

Palm, et al., Macroporous Polyacrylamide/Poly(ethylene glycol) Matrixes as Stationary Phases in Capillary Electrochromatography, *Analytical Chemistry,* vol. 69, No. 22, Nov. 15, 1997, pp. 4499–4507.

Hayes, et al., "Sol–Gel Monolithic Columns with Reversed Electroosmotic Flow for Capillary Electrochromatography," *Analytical Chemistry,* vol. 72, No. 17, Sep. 1, 2000, pp. 4090–4099.

Mol et al., "Trace Level Analysis of Micropollutants in Aqueous Samples using Gas Chromatography with On–Line Sample Enrichment and Large Volume Injection," *Journal of Chromatography A,* 703 (1995) pp. 277–307.

Quirino, et al., "Approaching a Million–Fold Sensitivity Increase in Capillary Electrophoresis with Direct Ultraviolet Detection: Cation–Selective Exhaustive Injection and Sweeping," *Analytical Chemistry,* vol. 72, No. 5, Mar. 1, 2000, pp. 1023–1030.

Rudge, et al., "Solute Retention in Electrochromatography by Electrically Induced Sorption," *AIChE Journal,* May 1993, vol. 39, No. 5, pp. 797–808.

Kitagawa, et al., "Voltage–Induced Sample Release from Anion Exchange Supports in Capillary Electrochromatography," *Analytical Sciences,* Jun. 1998, vol. 14, pp. 571–575.

Josic, et al., "Monoliths as Stationary Phases for Separation of Proteins and Polynucleotides and Enzymatic Conversion," *Journal of Chromatography B,* 752 (2001) pp. 191–205.

Peters, et al., "Molded Rigid Polymer Monoliths as Separation Media for Capillary Electrochromatography," *Analytical Chemistry,* vol. 69, No. 17, Sep. 1, 1997.

Dulay, et al., "Automated Capillary Alectrochromatography: Reliability and Reproducibility Studies," *Journal of Chromatography A,* 725 (1996) pp. 361–366.

Brinker, et al., "Sol–Gel Science: The physics and Chemistry of Sol–Gel Processing," *Academic Press,* San Diego, pp. 372–385, 408–411, 458–459 1990.

Badini, et al., "Impregnation of a pH–Sensitive Dye into Sol–Gels for Fibre Optic Chemical Sensors," *Analyst, 120,* pp. 1025–1028, Apr. 1995.

Snyder, Introduction to Modern Liquid Chromatography, *John Wiley & Sons, Inc.,* New York, 1979, pp. 145–147.

International Search Report mailed Oct. 25, 2002?.

Boughtflower et al., "Capillary Electrochromatography—Some Important Considerations in the Preparation of Packed Capillaries and the Choice of Mobile Phase Buffers," *Chromatographia,* vol. 40, No. 5/6, Mar. 1995, pp. 329–335.

Copy of International Search Report mailed Jan. 3, 2003.

Chong et al., "Sol–Gel Coating Technology for the Preparation of Solid–Phase Microextraction Fibers of Enhanced Thermal Stability," *Analytical Chemistry,* vol. 69, No. 19, Oct. 1, 1997, pp. 3889–3898.

Righetti et al., "'Laterally Aggregated' Polyacrylamide Gels for Electrophoresis," *Electrophoresis,* 13, 1992, pp. 587–595.

Righetti et al., "On the Limiting Pore Size of Hydrophilic gels for Electrophoresis and Isoelectric Focusing," *Journal of Biochemical and Biophysical Methods,* 4, 1981, pp. 347–363.

Guo et al., "Modification of the Inner Capillary Surface by the Sol–Gel Method: Application to Open Tubular Electrochromatography," *J. Microcolumn Separations,* vol. 7, No. 5, 1995, pp. 485–491.

Burgi et al., "Optimization in Sample Stacking for High–Performance Capillary Electrophoresis," *Anal. Chem.* 1991, 63, pp. 2042–2047.

Etienne et al., "Photocurable Sol–Gel Coatings: Channel Waveguides for Use at 1.55 $\mu$m," *Journal of Sol Gel Science and Technology,* 13, 1998, pp. 523–527.

Guo et al., "Hydrolytically Stable Amino–Silica Glass Coating Material for Manipulation of the Electroosmotic Flow in Capillary Electrophoresis," *Journal of Chromatography A,* 744, 1996, pp. 17–29.

Horak et al., "The Effect of Polymeric Porogen on the Properties of Macroporous Poly(glycidyl) Methacrylate–co– ethylene Dimethacrylate)," *Polymer,* vol. 34, No. 16, 1993, pp. 3481–3489.

Kenny et al., "Micropreparative Capillary Electrophoresis (MPCE) and Micropreparative HPLC of Protein Digests," *Techniques in Protein Chemistry IV,* pp. 363–370.

Smith et al., "Micropreparative Separation of Tryptic Digests by Capillary Electrophoresis and Characterization by Protein Sequencing," *Techniques in Protein Chemistry III,* pp. 113–120.

Swartz et al., "On–Line Sample Preconcentration on a Packed–Inlet Capillary for Improving the Sensitivity of Capillary Electrophoretic Analysis of Pharmaceuticals," *Journal of Chromatography,* 632, 1993, pp. 209–213.

Tsuda et al., "Rectangular Capillaries for Capillary Zone Electrophoresis," *Anal. Chem.,* 62, 1990, pp. 2149–2152.

\* cited by examiner

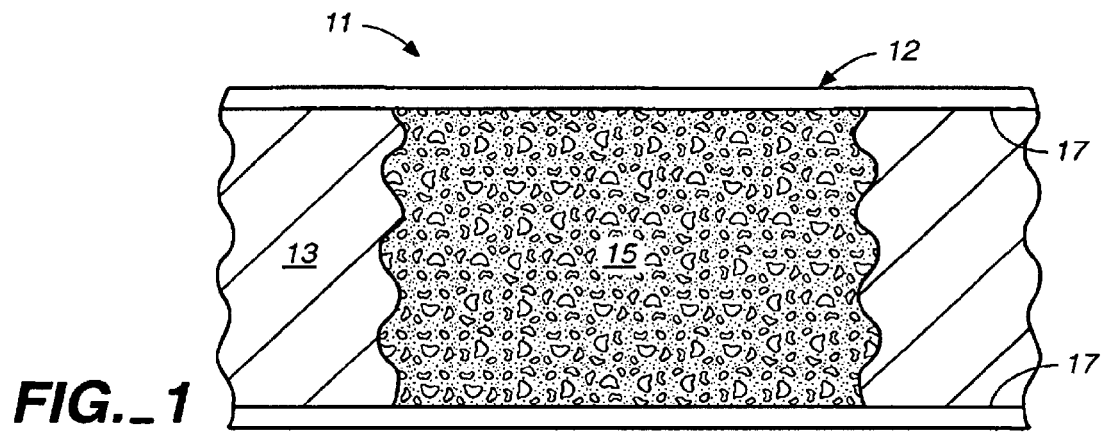
FIG._1
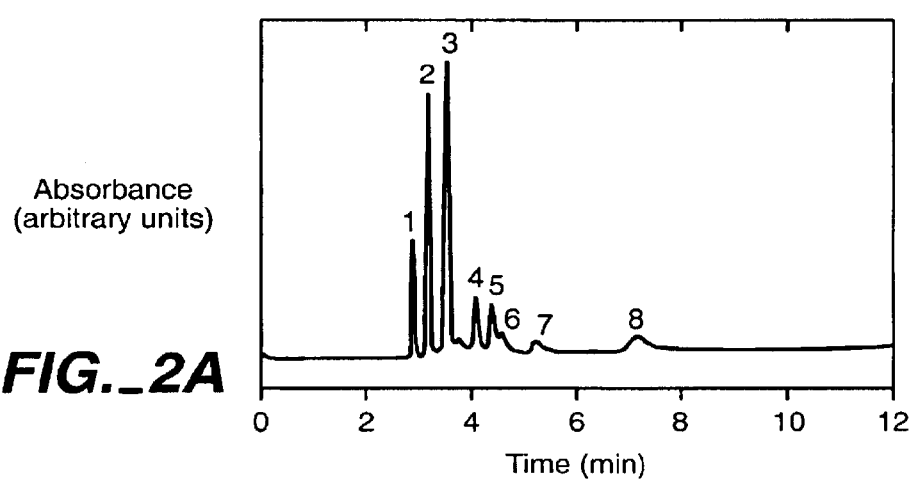
FIG._2A
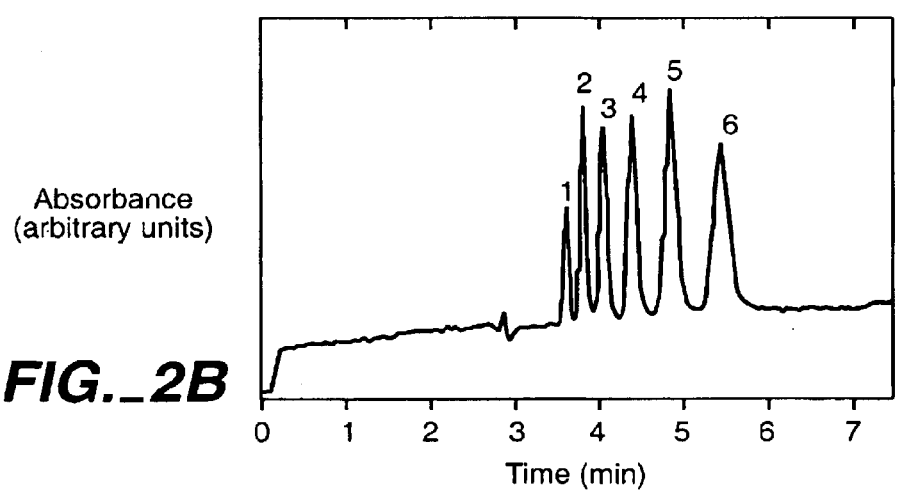
FIG._2B

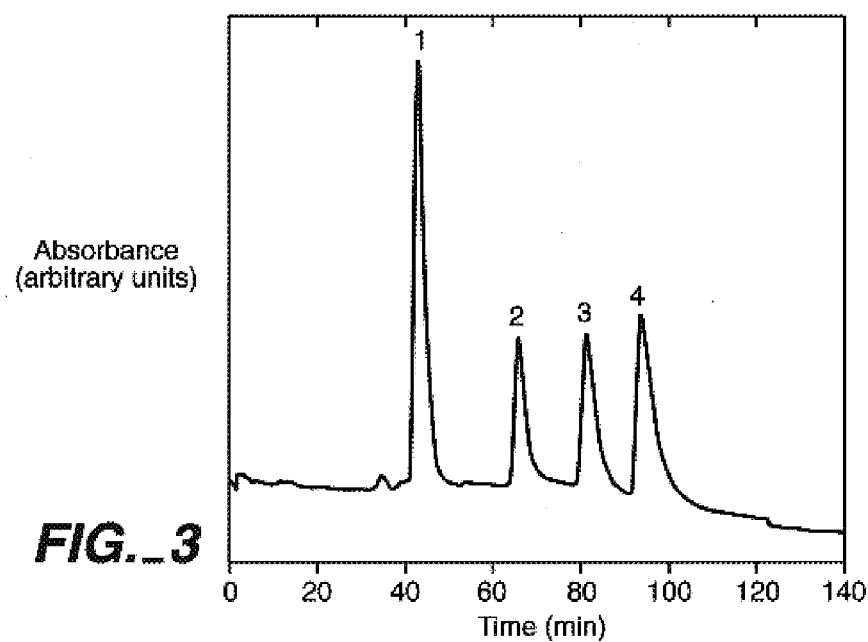
FIG._3
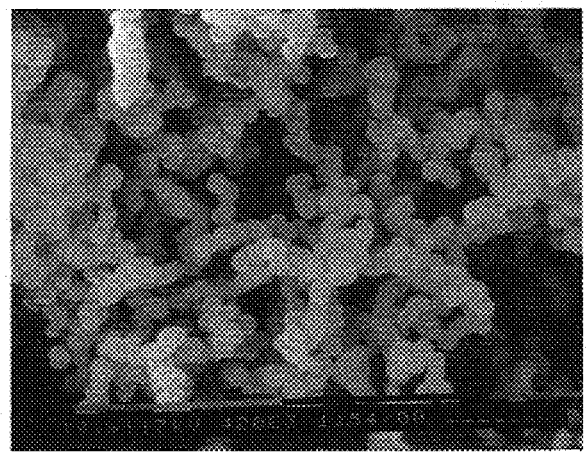
FIG._4A
FIG._4B

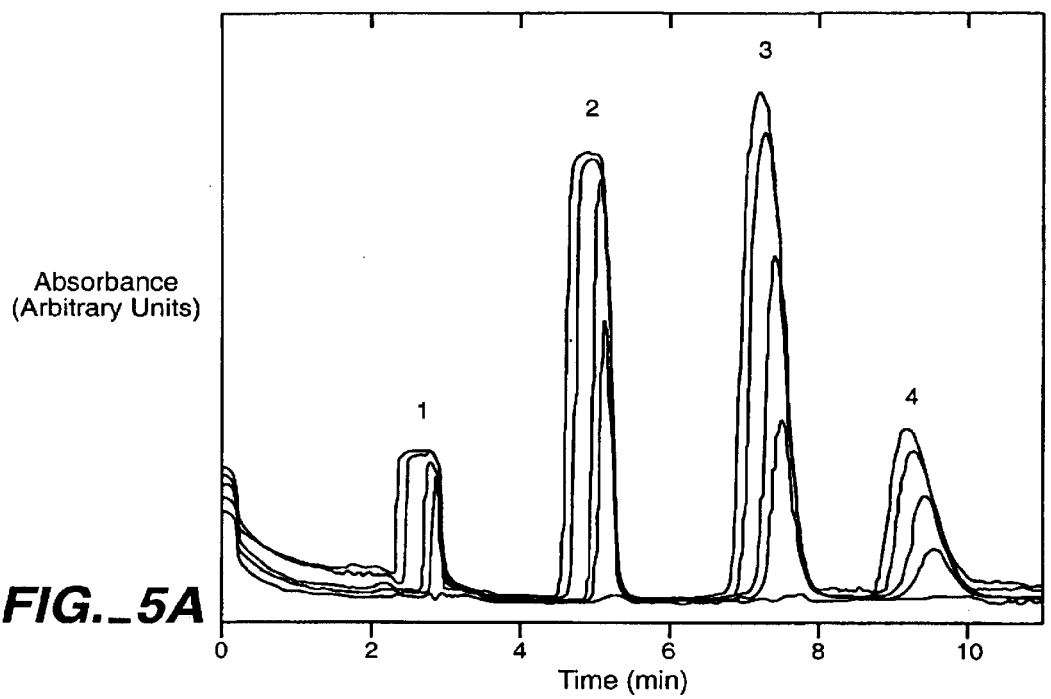
FIG._5A
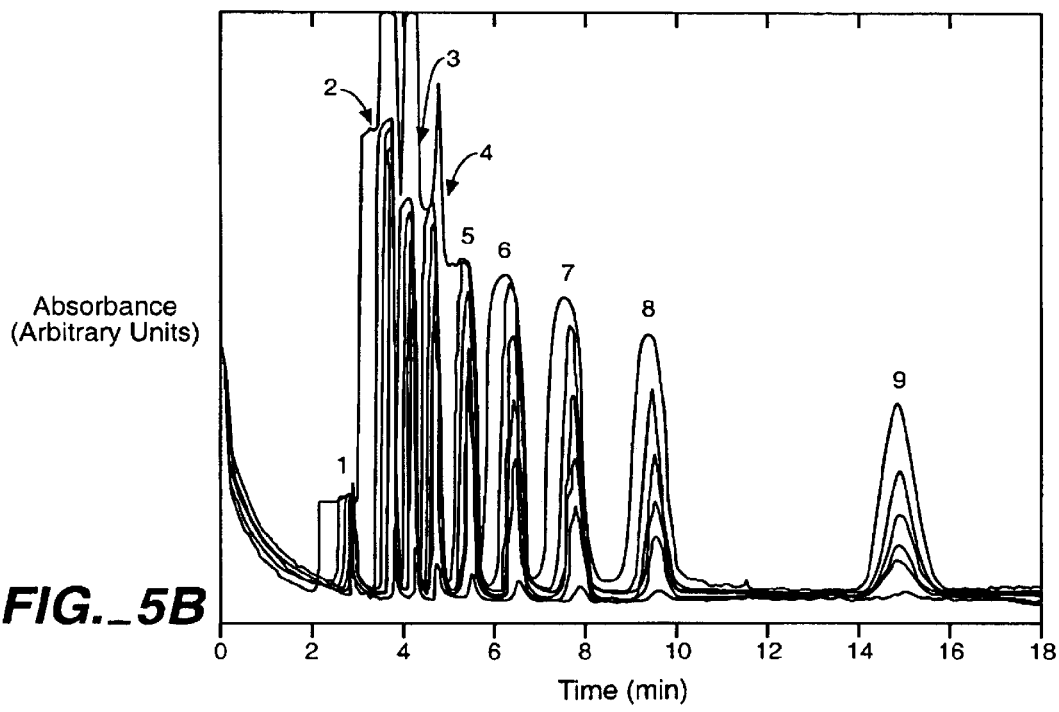
FIG._5B

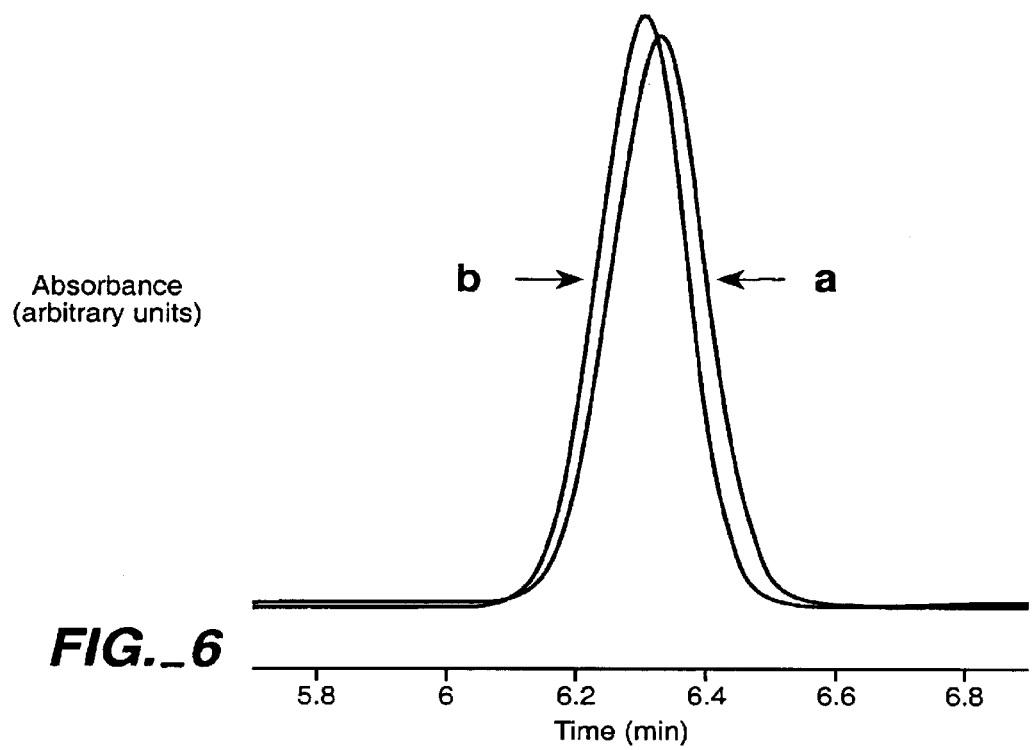
FIG._6
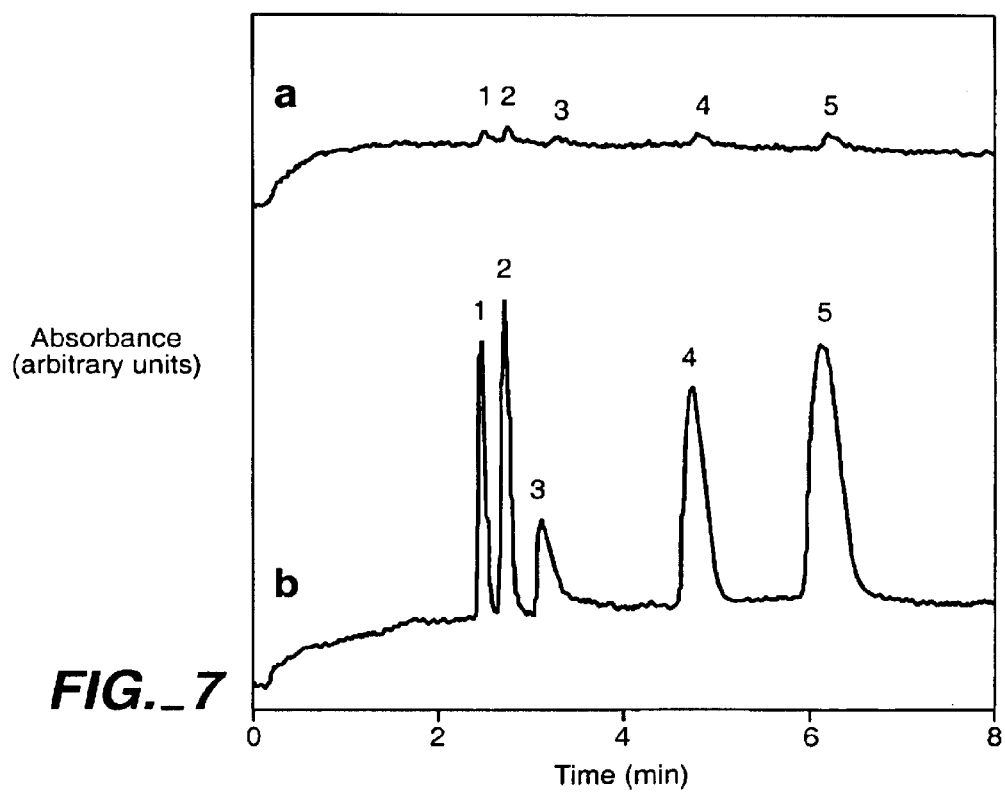
FIG._7

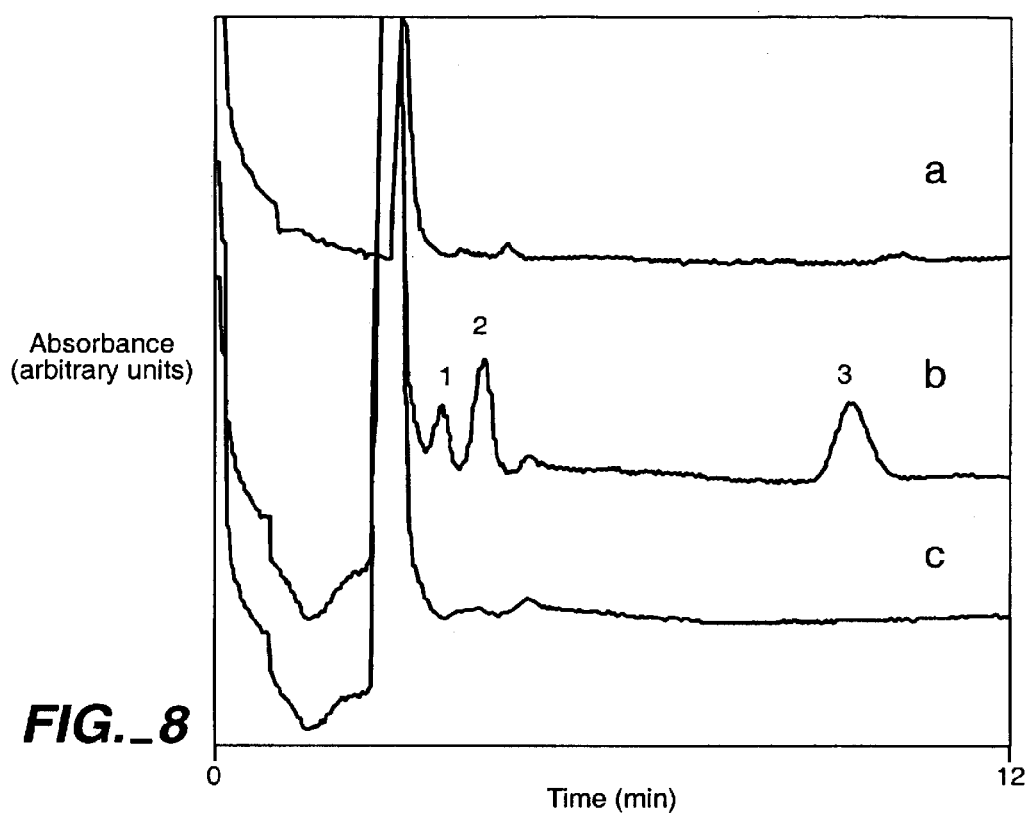
FIG._8

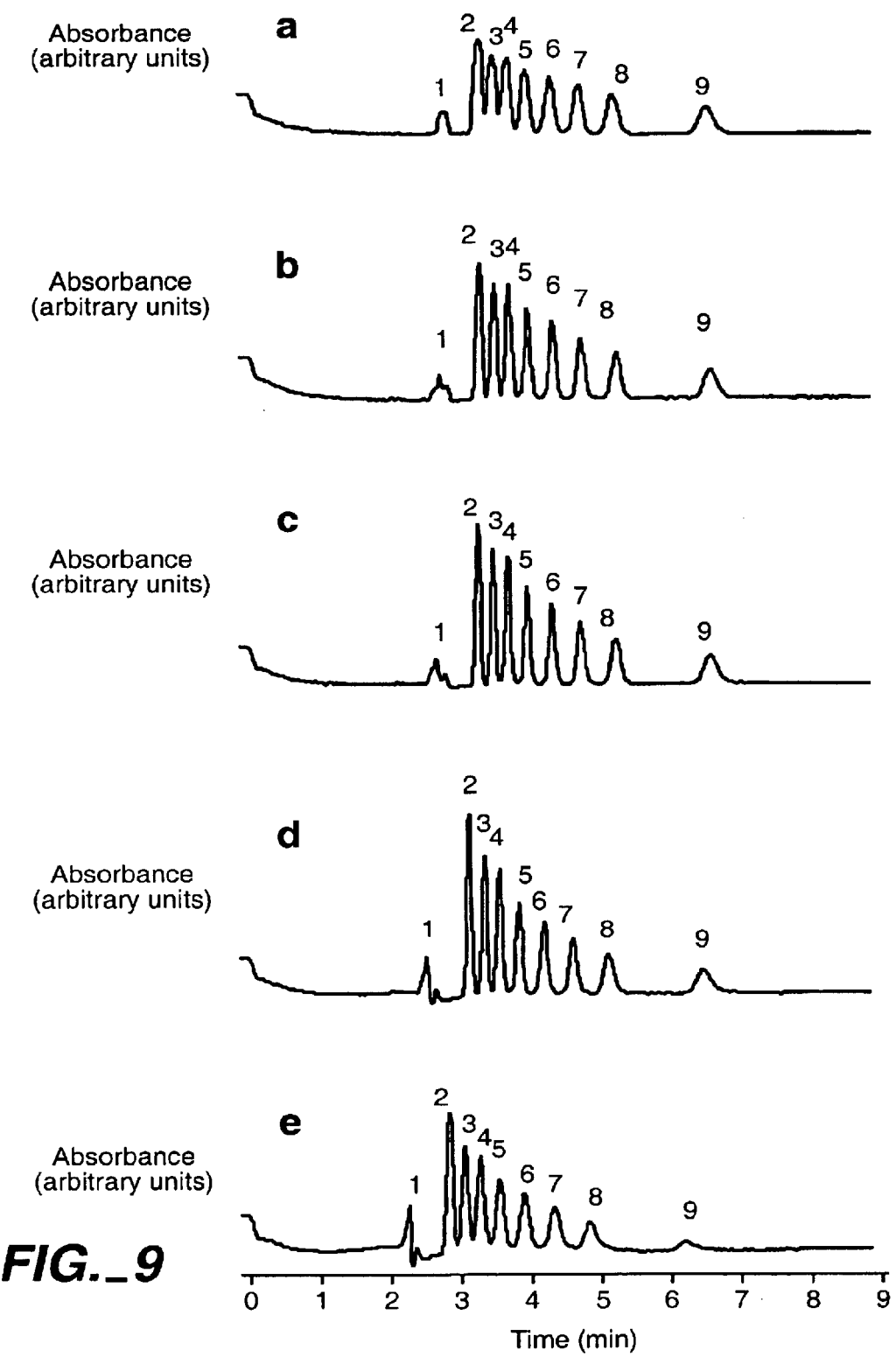
FIG._9

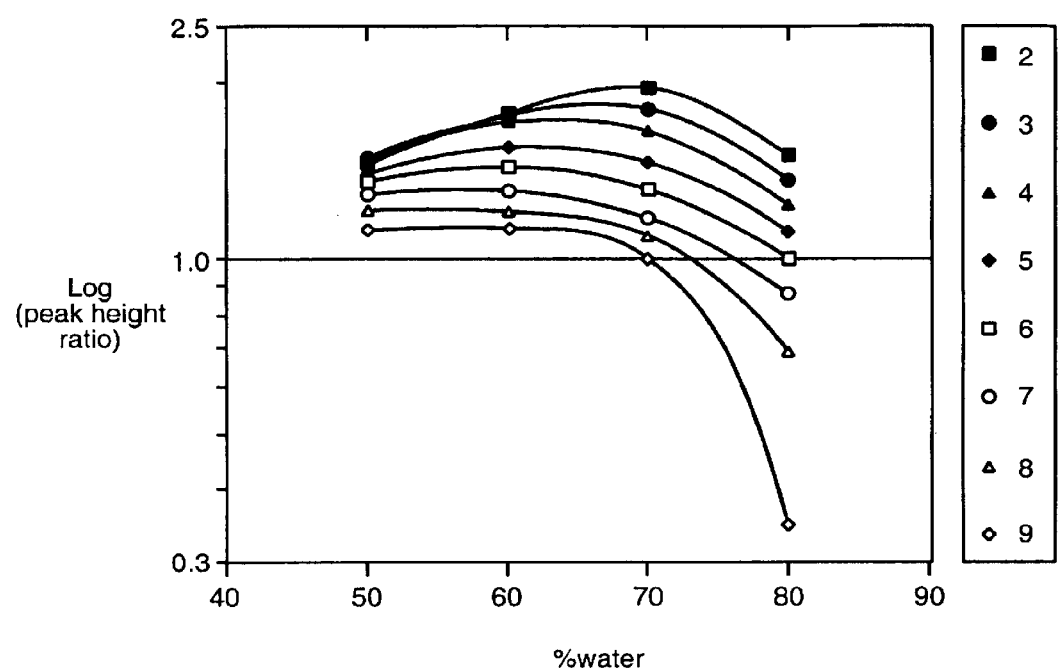
FIG._10

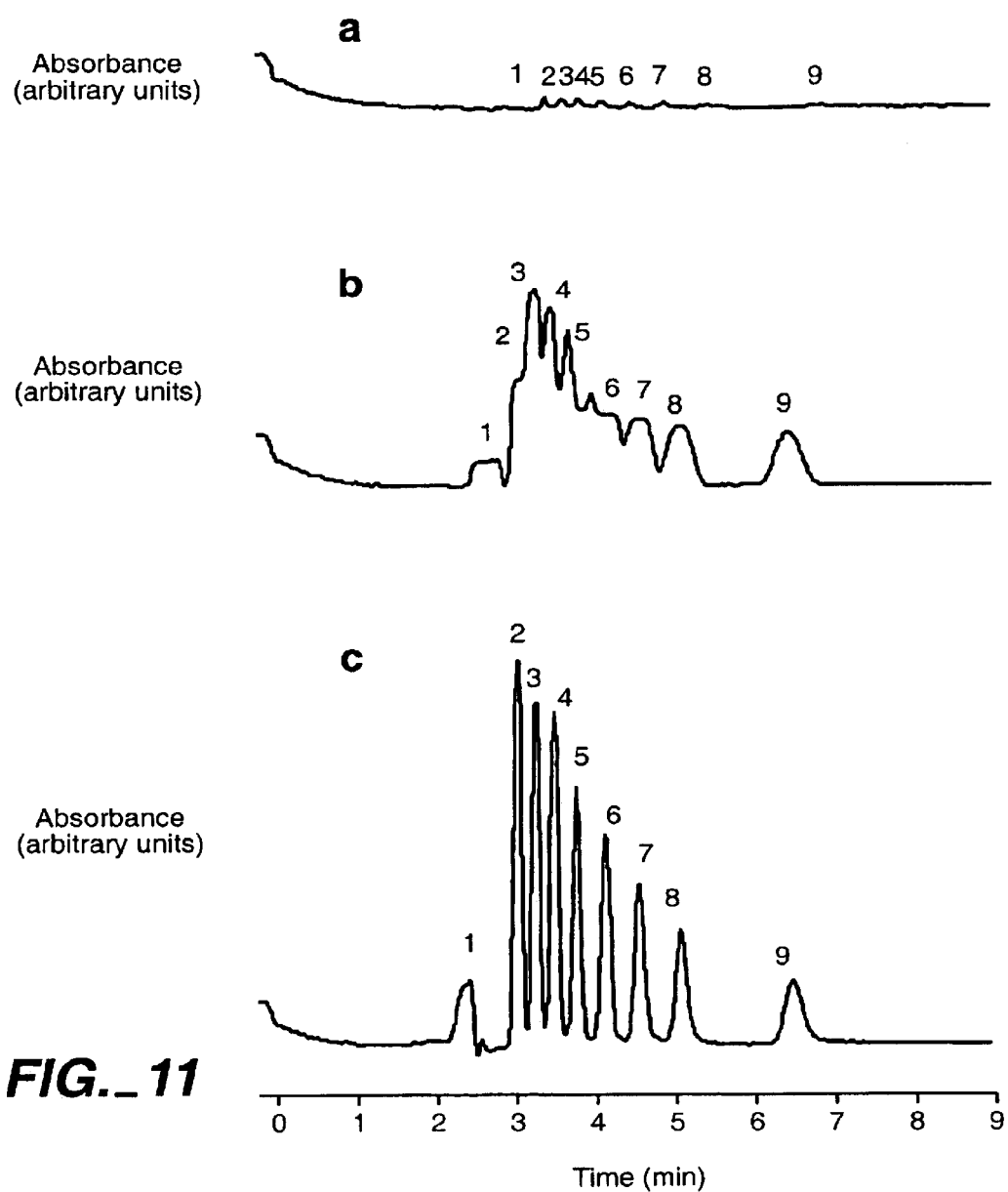
FIG._11

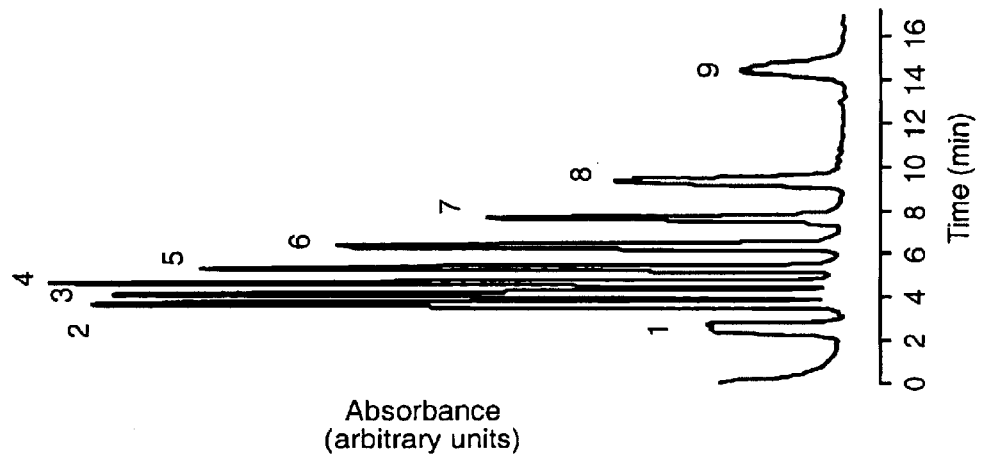
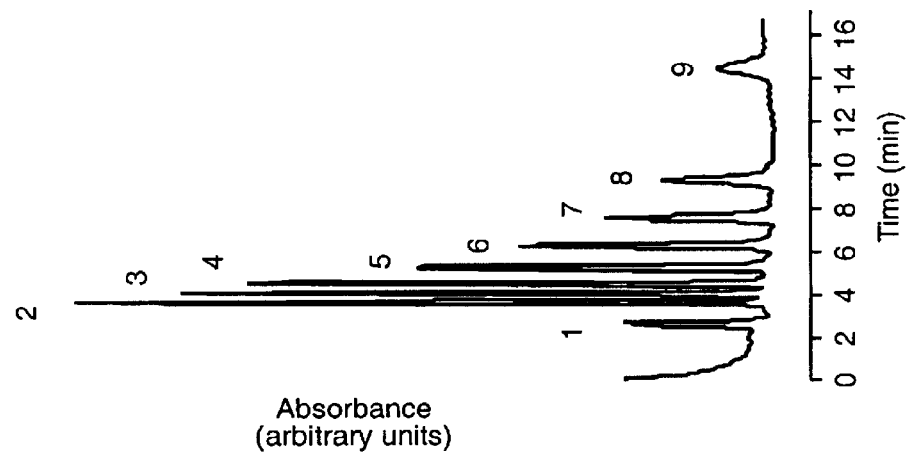
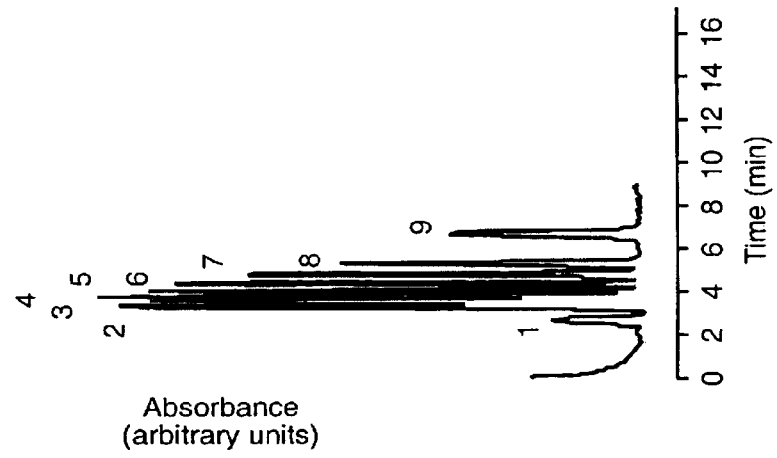

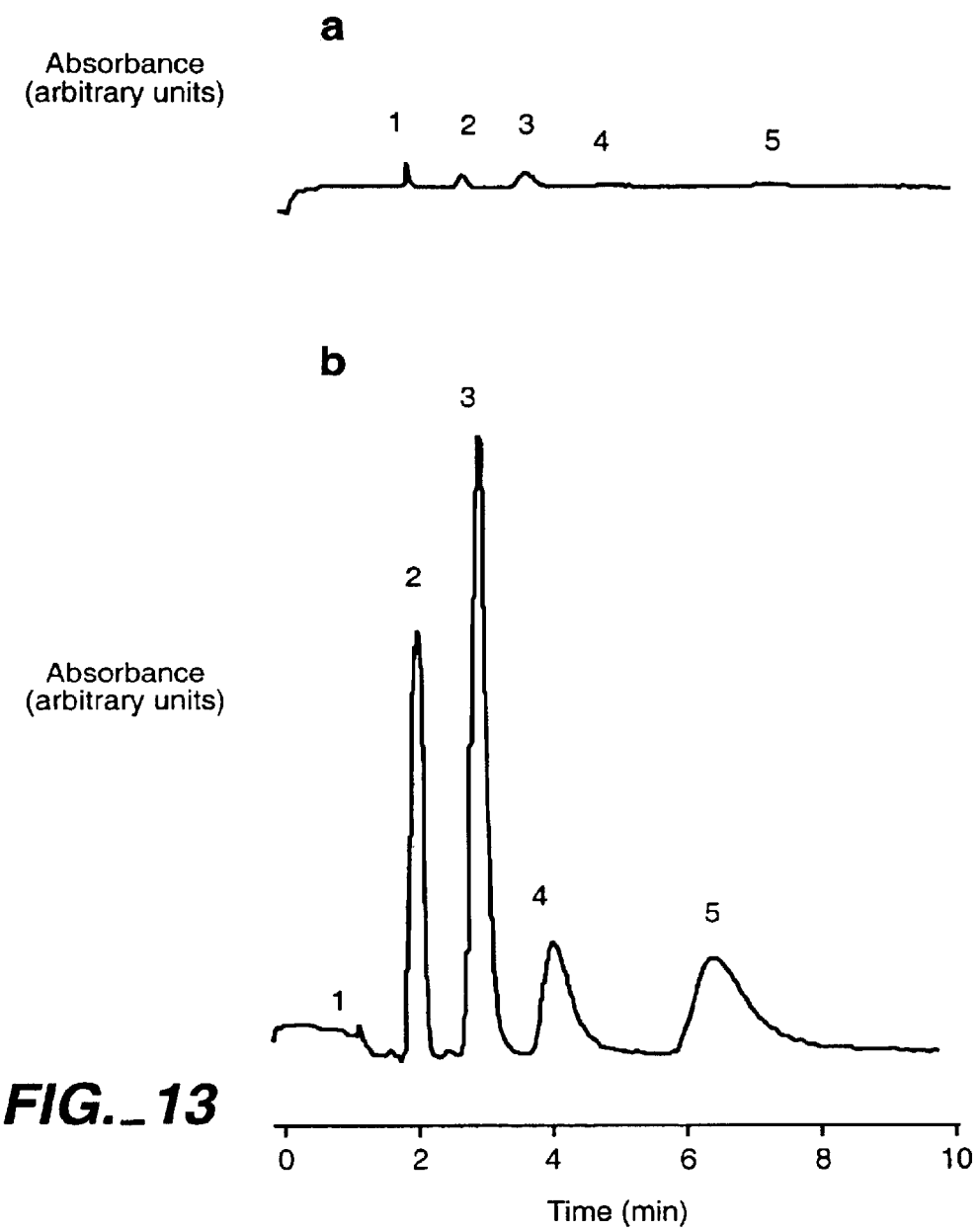
FIG._13

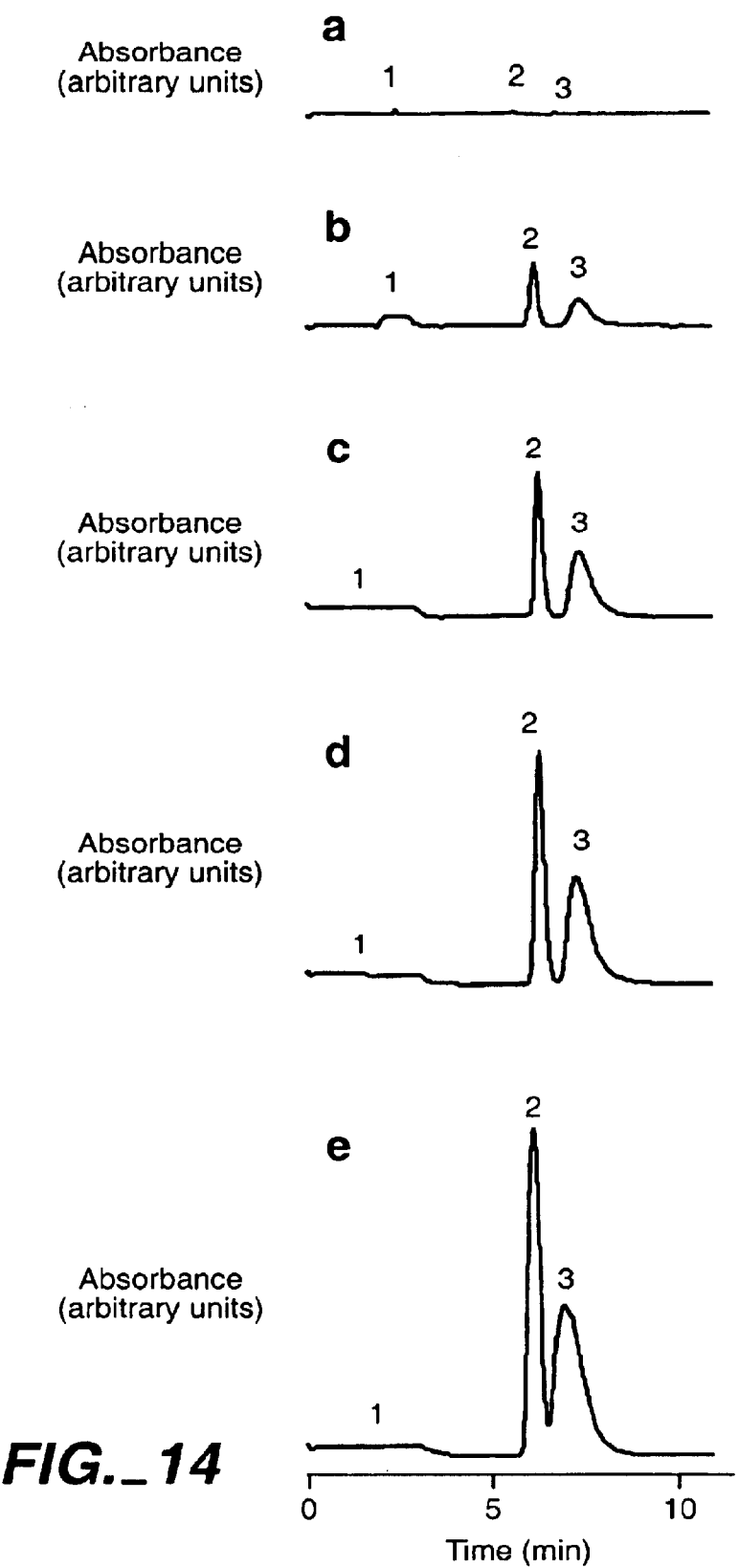
FIG._14

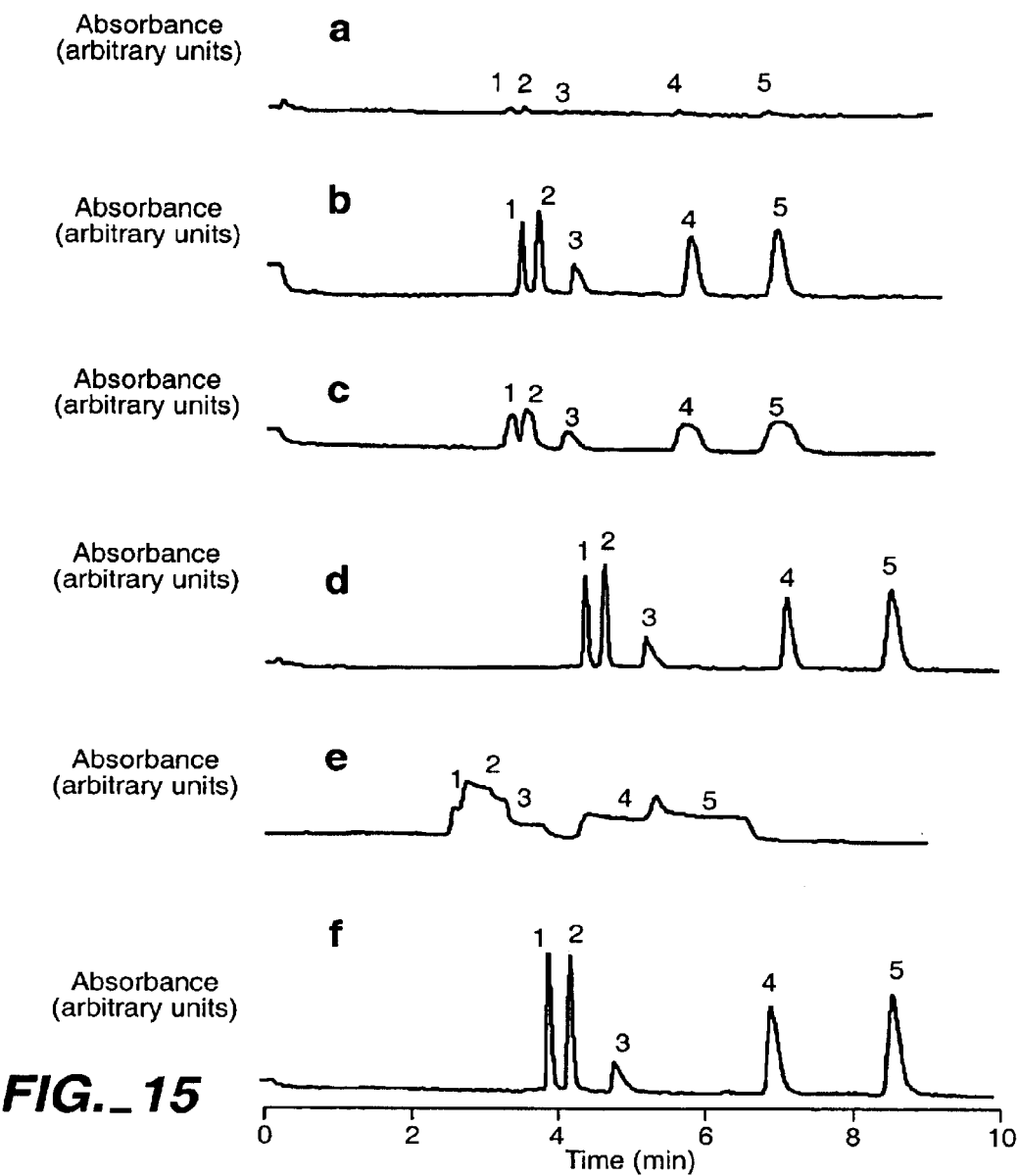
FIG._15

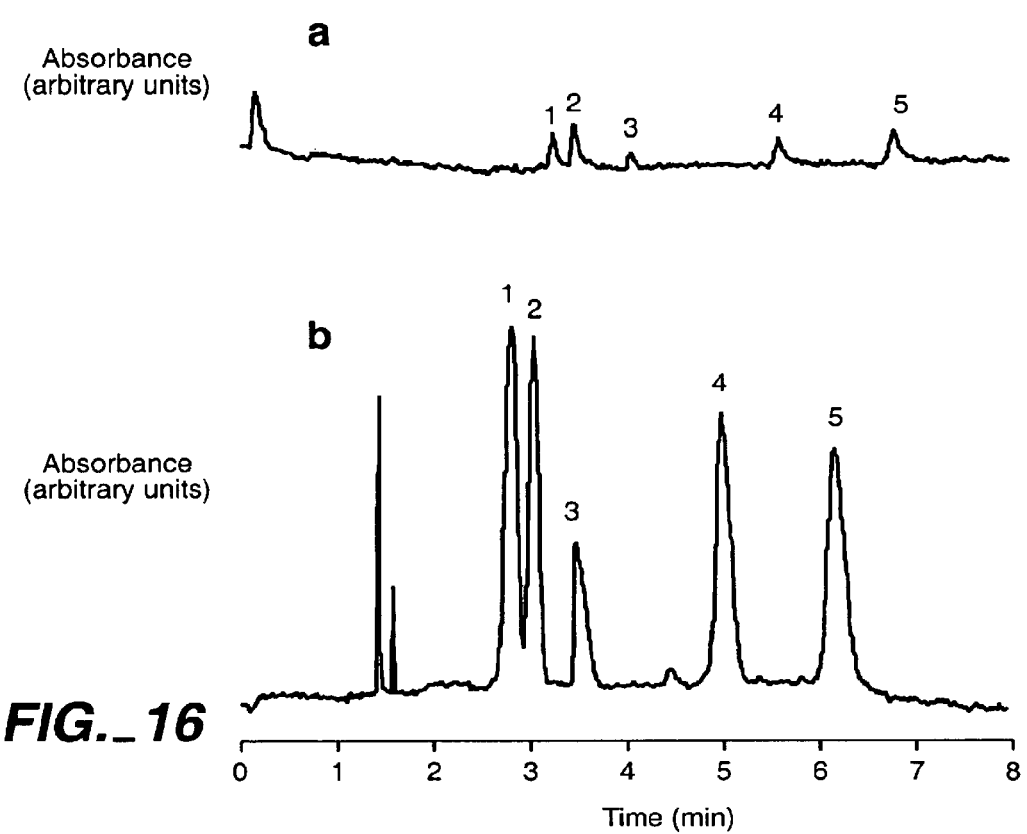
FIG._16

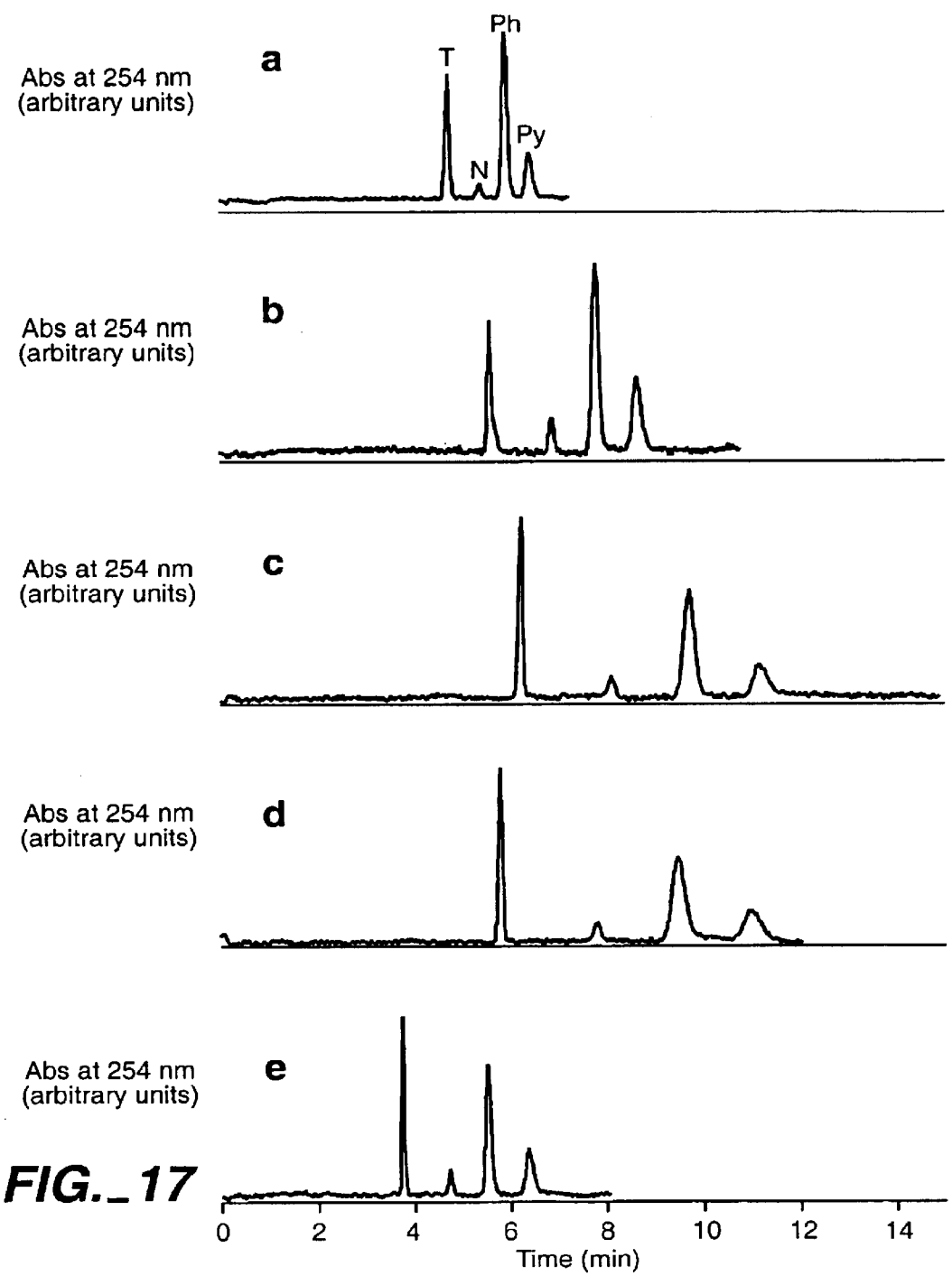
FIG._17

PHOTOPOLYMERIZED SOL-GEL COLUMN AND ASSOCIATED METHODS

BACKGROUND OF THE INVENTION

The invention relates in general to a separation column, and, in particular, to a photopolymerized sol-gel column.

Capillary electrochromatography (CEC) has been regarded as a very promising analytical separation technique that combines the efficiency of capillary zone electrophoresis (CZE) with the selectivity of liquid chromatography. Although CEC has been applied in many different areas, packed-column preparation and low-detection sensitivity remain challenges of this technique. Capillary columns containing small silica packings have been the mainstay of CEC. One disadvantage of packed columns is the fabrication of porous frits of controlled pore sizes, lengths, and high mechanical stabilities. In response to frit fabrication problems, surface-functionalized open-tubular capillary columns and monolithic capillaries are being developed as variants of packed capillary columns. Monolithic capillary columns have received much attention because of the advantages offered in the control of permeability and surface charge.

A major challenge in CEC techniques is the detection of samples containing analytes at low concentration. The lack of sensitivity at low concentration stems from the small sample volume and the short optical path length for on-line detection. Dedicated sample preparation schemes that enrich the target analytes before sample injection are often necessary in order to obtain the necessary sensitivity for many real-world analyses. Schemes such as solvent-solvent extraction and solid-phase extraction are often very tedious and time-consuming.

An alternative to these schemes is on-line preconcentration. In gas chromatography, this goal is met by passing a gas stream through a cold column that is subsequently heated. In high-performance liquid chromatography (HPLC), this process is usually done by gradient HPLC in which the analytes are retained on the column much more strongly for the first solvent than for succeeding ones. On-line preconcentration has also enjoyed some success in electrophoretic separations. For example, in capillary electrophoresis (CE), these include isotachophoresis, sample stacking, sweeping, and the use of a dynamic pH junction. In CZE, F. E. P. Mikkers, F. M. Everaerts, P. E. M. Verheggen, *J. Chromatogr.* 169 (1979), pp. 1–10 and R. L. Chien, D. S. Burgi, *Anal. Chem.* 64 (1992) pp. 489A–496A, demonstrated that changes in electric field strength between sample and background solution zones can focus (i.e., stack) charged species. In electrokinetic chromatography, J. P. Quirino, S. Terabe, *Science,* 282 (1998) pp. 465–68 and J. P. Quirino, S. Terabe, *Anal. Chem.* 71(8) (1999) pp. 1638–44, have shown that micelles can act to concentrate (i.e., sweep) neutral and charged species.

In CEC using particle (e.g., octadecyl silica) packed columns, focusing effects similar to that in gradient high performance liquid chromatography have been reported. These focusing effects were achieved using (1) step-gradient elution, (2) preparation of the sample in a noneluting solvent, or (3) injection of a water plug after sample injection. In M. R. Taylor, P. Teale, D. Westwood, D. Perrett, *Anal. Chem.* 69 (1997) pp. 2554–58, the authors were the first to report the use of a step-gradient for the preconcentration of steroidal samples in 1997. In D. A. Stead, R. G. Reid, R. B. Taylor, *J. Chromatogr. A* 798 (1998) pp. 259–67, the authors achieved a 17-fold increase in the detection sensitivity of a mixture of steroids by preconcentration using a noneluting sample matrix. In Y. Zhang, J. Zhu, L. Zhang, W. Zhang, *Anal. Chem.* 72 (2000) pp. 5744–47, the authors also used a noneluting solvent for the preconcentration of benzoin and mephenytoin by a factor of 134 and 219, respectively. In C. M. Yang, Z. El Rassi, *Electrophoresis* 20 (1999) pp. 2337–42, the authors reported on the preconcentration of a dilute sample of pesticides using a short plug of water injected after a long plug of sample. In M. J. Hilhorst, G. W. Somsen, G. J. de Jong, *Chromatographia* 53 (2001) pp. 190–96, the authors demonstrated preconcentration of structurally related steroids using a noneluting matrix and step-gradient elution. A gain in sensitivity of 7 to 9 times was reported. Similarly, in T. Tegeler, Z. El Rassi, *Anal. Chem.* 73(14) (2001) pp. 3365–72, the authors just recently reported preconcentration of analytes in a mixture of carbamate insecticides using a combination of a noneluting matrix and step-gradient elution. The maximum allowable sample plug length was ~20 cm and a 500-fold sensitivity increase is achieved for carbofuran. A further increase in detection sensitivity was achieved by Zhang co-workers, who combined field-enhanced sample injection with solvent gradient elution. They demonstrated a 17,000-fold increase in peak height for a positively charged analyte, propatenene.

It is desirable to provide a separation column with improved characteristics and that is easy to make.

SUMMARY OF THE INVENTION

A separation column includes a separation channel and a fritless separation medium in the channel. The medium includes a porous matrix, and the porous matrix includes a metal organic polymer. The polymer may be a photopolymer. In the preferred embodiment, the porous matrix contains no chromatographic particles. The porous matrix may be used to both preconcentrate and separate analytes without chromatographic particles. The separation column allows for the concentration and separation of larger volumes of analytes than a separation column with chromatographic particles.

A method of preparing a monolith is provided. A separation column is provided. A mixture is introduced into the separation column. The mixture includes a metal organic compound. The mixture is irradiated to form a solid, porous matrix via photoinitiated polymerization. Thus, a fritless separation medium is formed in the separation column. In the preferred embodiment, the porous matrix contains no chromatographic particles. Preparation of a fritless separation medium without chromatographic particles is simpler than preparing a separation medium with a frit or chromatographic particles. The porous matrix may be used both to preconcentrate and separate analytes.

The photochemical route to the preparation of the porous matrix has many advantages: (1) short preparation time, (2) control of the pore size, (3) control over the placement and length of the porous matrix, (4) high mechanical strength, and (5) avoidance of high temperatures that lead to cracking.

A method of separating a sample of analytes is provided. A separation column including a separation channel and a fritless separation medium in the channel is provided. The medium includes a porous matrix, and the porous matrix includes a metal organic polymer, such as a photopolymer. In the preferred embodiment, the porous matrix contains no chromatographic particles. A sample of analytes carried in a solution is introduced through the column. The medium concentrates the analytes on the column. A solution is caused to flow through the column, thereby separating and eluting the analytes. The medium both preconcentrates and separates the analytes. In addition to the effect exerted by the medium, preconcentration can be further enhanced by a solvent gradient or sample stacking.

BRIEF DESCRIPTION OF THE DRAWINGS

The above and other features and aspects of the present invention will become more apparent upon reading the following detailed description in conjunction with the accompanying drawings, in which:

FIG. 1 is a schematic longitudinal view of a separation column, according to an embodiment of the present invention;

FIGS. 2A and 2B are two representative electrochromatograms showing a plot of absorbance versus retention time for (a) one column and (b) another column, using an embodiment of the present invention;

FIG. 3 is a representative electrochromatogram showing a plot of absorbance versus retention time using an embodiment of the present invention;

FIGS. 4A and 4B are SEM micrographs of embodiments of the present invention;

FIGS. 5A and 5B are representative electrochromatograms showing plots of absorbance versus retention time for different analytes using embodiments of the present invention;

FIG. 6 is a representative electrochromatogram showing a plot of absorbance versus retention time using an embodiment of the present invention;

FIG. 7 (panels a and b) are representative electrochromatograms showing plots of absorbance versus retention time using an embodiment of the present invention;

FIG. 8 (panels a, b, and c) are representative electrochromatograms showing plots of absorbance versus retention time using an embodiment of the present invention;

FIG. 9 (panels a, b, c, d, and e) are representative electrochromatograms showing plots of absorbance versus retention time using an embodiment of the present invention;

FIG. 10 is a graphical representation showing a plot of the logarithm of peak height ratio versus the percentage of water in a sample using an embodiment of the present invention;

FIG. 11 (panels a, b, and c) are representative electrochromatograms showing plots of absorbance versus retention time using an embodiment of the present invention, FIGS. 12A, 12B, and 12C are representative electrochromatograms showing plots of absorbance versus retention time using an embodiment of the present invention;

FIG. 13 (panels a and b) are representative electrochromatograms showing plots of absorbance versus retention time using an embodiment of the present invention;

FIG. 14 (panels a, b, c, d, and e) are representative electrochromatograms showing plots of absorbance versus retention time using an embodiment of the present invention;

FIG. 15 (panels a, b, c, d, e, and f) are representative electrochromatograms showing plots of absorbance versus retention time using an embodiment of the present invention;

FIG. 16 (panels a and b) are representative electrochromatograms showing plots of absorbance versus retention time using an embodiment of the present invention; and FIG. 17 (panels a, b, c, d, and e) are representative electrochromatograms showing plots of absorbance versus retention time using an embodiment of the present invention.

For simplicity of description, like reference symbols are used for like or similar parts in this application.

DETAILED DESCRIPTION OF THE EMBODIMENTS

FIG. 1 is a longitudinal cross-sectional view of a separation column, according to an embodiment of the present invention. The separation column 11 includes a separation channel 13 in tube 12 and a separation medium 15 in the channel 13. The separation column 11 may be a capillary or a planar chip, and the separation channel 13 may include a detection window. The separation medium 15 fills at least a section of the channel 13. The medium 15 is homogeneous and preferably does not have frits or chromatographic particles. The medium 15 may be attached to a channel wall 17 of the channel 13. Preferably, the medium 15 may be covalently bound to the channel wall 17.

Tube 12 can have many different cross-sections, such as a circular cross-section. Alternatively, tube 12 can have an elongated cross-section. These and other cross-sections are possible for tube 12 and are within the scope of the invention. Tube 12 may be a round capillary typically made of fused silica. The inside diameter (i.d.) of the capillary may be from about 10 $\mu$m to about 1000 $\mu$m, preferably from about 75 $\mu$m to about 500 $\mu$m. Tube 12 may be a planar chip or a confined space, such as a column confined by two sheets.

The medium 15 includes porous matrix, and the porous matrix includes a metal organic, or metalorganic, polymer, such as a photopolymer, wherein the term metal organic, or metalorganic, refers to a material that comprises an organic ligand attached to a metal atom or a metalloid atom. (See Brinker, C. Jeffrey et al., Sol-Gel Science, The Physics and Chemistry of Sol-Gel Processing, p. 2 (1990).) A precursor of the polymer may be a metal alkoxide, wherein the term metal alkoxide refers to a metal organic, or metalorganic, material, that has a metal-oxygen-carbon linkage or metalloid-oxygen-carbon linkage. (Id.) Herein, where "metal" is used in connection with a metal organic, or metalorganic, material, or in connection with a metal alkoxide, it encompasses metals and metalloids. The metal or metalloid may be aluminum, barium, antimony, calcium, chromium, copper, erbium, germanium, iron, lead, lithium, phosphorus, potassium, silicon, tantalum, tin, titanium, vanadium, zinc, or zirconium. The precursor may include a photoactive group, such as methacrylate. In one embodiment, the precursor may be trimethoxysilylpropyl methacrylate, also known as methacryloxypropyltrimethoxy silane.

Different functionalized or derivatized monomers can be used to prepare a porous matrix 15 with different physical properties, such as pore size, polymer charge density, and hydrophobicity. Control of the pore shapes and sizes through the use of different porogens can result in a porous matrix with a wide distribution of pore sizes (i.e., pore-size gradient). A porous matrix with a pore-size gradient can function as "molecule sorter" in capillary electrophoresis and capillary electrochromatography. The porous matrix 15 can separate a mixture of large molecules whose size structures or chemistries (e.g., DNA fragments) may differ. In addition, separation columns 11 can be designed for reversed-phase, size-exclusion, affinity, ion-exchange chromatographies, etc.

A porous matrix 15 may be a mixed phase porous matrix prepared from a mixture of monomers. For example, the monomers may include methacryloxypropyltrimethoxy silane, bis(triethoxysilyl)ethane, and bis(triethoxysilyl)octane. The mixed phase porous matrix may have different properties, such as hydrophobicity.

The porous matrix has an affinity for analytes and can be used to both preconcentrate and separate a sample of analytes. The affinity for an analyte may be described by the retention factor, k, of the analyte. The retention factor, k, is equal to $$k = \frac{\text{amount of component in stationary phase}}{\text{amount of component in mobile phase}} \quad (1)$$

The retention factor, k, may also be expressed as $$k = \frac{t_R - t_O}{t_O} \quad (2)$$

where $t_R$ is the migration time of the analyte, and $t_O$ is the migration time of an "unretained" analyte. The retention factor is affected by the nature of the solvent, the nature of the analyte, the length of the column, the permeability of the porous matrix, the hydrophobicity of the porous matrix, and the detailed morphology of the porous matrix.

The separation column 11 may be used for analytic or semipreparative work. Separation of analytes in the submilligram to milligram quantities may become possible with preconcentration on separation columns 11. For example, more than about 100-nL of sample solution at analyte concentrations in the mM levels can be injected into the column without significant evidence of overloading.

A method of preparing a monolith in the separation column 11 is provided. A separation column is provided. The separation column may be a round capillary typically made of fused-silica. The inside diameter (i.d.) of the capillary may be from about 10 μm to about 1000 μm, preferably from about 75 μm to about 500 μm.

A mixture that includes a metal organic compound is introduced into the separation column. The mixture forms a solid, porous matrix via photoinitiated polymerization. The mixture may comprise a metal organic monomer, a porogen, and a photoinitiator. The metal organic monomer may be a metal alkoxide, such as a silane, or a mixture of metal alkoxides. The metal may be aluminum, barium, antimony, calcium, chromium, copper, erbium, germanium, iron, lead, lithium, phosphorus, potassium, silicon, tantalum, tin, titanium, vanadium, zinc, or zirconium. The metal alkoxide may include a photoactive group, such as methacrylate. In one embodiment, the precursor may be trimethoxysilylpropyl methacrylate, also known as methacryloxypropyltrimethoxy silane. In another embodiment, the precursor may be a mixture of methacryloxypropyltrimethoxy silane and another precursor, such as bis(triethoxysilyl)ethane or bis(triethoxysilyl)octane.

The metal organic monomer may be added to an acid or base catalyst for the hydrolysis of the precursor. The catalyst converts the alkoxy groups to hydroxyl groups. For example, a silane may undergo the following hydrolysis reaction to form a fully hydrolyzed silane:

$$Si(OR)_4 + 4H_2O \rightarrow Si(OH)_4 + 4ROH \quad (3).$$

The hydrolysis reaction may stop at a partially hydrolyzed silane, $Si(OR)_{4-n}(OH)_n$. The metal organic monomer and the catalyst may be stirred for about zero minutes to about twenty-four hours.

A porogen or a mixture of porogens may be mixed with the metal organic monomer and the catalyst, and the mixture may be stirred for about zero minutes to about twenty-four hours. During this time, the metal organic monomer may undergo a condensation reaction to form dimers, trimers, and other oligomers. For example, a partially hydrolyzed silane may undergo the following condensation reaction:

$$2(RO)_3SiOH \rightarrow (RO)_3Si\text{—}O\text{—}Si(OR)_3 + H_2O \quad (4).$$

Larger oligomers may be formed by increasing the temperature of the reaction.

The porogen provides a molecular template to form pores within the matrix. For example, the porogen may be a solvent, such as toluene or a 1:1 mixture of hexane and toluene, a polymer, or an inorganic salt, such as sodium chloride powder or sodium sulfate. The polymeric porogen may be poly(methyl methacrylate) or polystyrene, as reported by D. Horak, J. Labsky, J. Pilar, M. Bleha, Z. Pelzbauer, F. Svec, *Polymer* 34(16) (1993) pp. 3481–89. The porogen may be selected controllably to form pores in the matrix 15. The porosity of the matrix may be controlled by the type of chemical (i.e., porogen) used and its volume or concentration in the reaction solution. For example, a molar or volume ratio of monomer to porogen may be selected to form pores in the mixture. By adjusting the molar ratio of the monomer and porogen, the physical properties (e.g., pore sizes) of the matrix may be controlled.

The photoinitiator or a photoactive group, such as methacrylate, on the monomer absorbs light to catalyze the polymerization of the metal organic compound. In one embodiment, the photoinitiator may be Irgacure 1800, available from Ciba Geigy, Tarrytown, N.Y.

If the separation column has an outer coating that is not transparent to the light source, the coating is first removed to make an irradiation window. The length of the coating will determine the length of the porous matrix formed within the separation column.

The fixture is introduced into the separation column. For example, the mixture may be flowed through the separation column using a syringe. The ends of the separation column may be sealed.

The mixture is irradiated, thereby forming a fritless, homogeneous separation medium in the separation column. For example, the separation column may be exposed to radiation for a short period of time, such as about five minutes. The wavelength of the radiation is dependent on the type of photoinitiator or photoactive group used in the reaction. The radiation may include visible or ultraviolet light. For example, radiation of 365 nm maybe used for the photoinitiator Irgacure 1800. The photoactive group methacrylate may be photopolymerized at a wavelength of 300 nm or 365 nm, as reported in C. Yu, F. Svec, J. M. J. Frechet, *Electrophoresis* 21(1) (2000) pp. 120–27 and H.-G. Woo, L.-Y. Hong, S.-Y. Kim, S.-H. Park, S.-J. Song, H.-S. Ham, *Bull. Korean Chem. Soc.* 16 (1995) pp. 1056–59, respectively.

A photochemical reaction occurs when the mixture is exposed to radiation. The photoinitator or photoactive group on the monomer absorbs the light to catalyze the polymerization of the metal organic compound.

The photochemical route to the preparation of a porous matrix has many advantages: (1) short preparation time, (2) control of the pore size, (3) control over the placement and length of the porous matrix, (4) high mechanical strength, and (5) avoidance of high temperatures that lead to cracking.

The separation medium preferably does not have frits or chromatographic particles, so the preparation of the separation medium is easier than preparation of a conventional separation medium with frits or chromatographic particles is.

Optionally, an organic solvent may be introduced into the separation column. For example, the organic solvent may be ethanol. The porous matrix may be washed clean of any unreacted material, the porogen, and the photoinitiator using an organic solvent. The solvent may be flowed through the separation column using a syringe or other means.

The separation column may be conditioned with a separation solution before using the column for separation. A separation solution may comprise a buffer, such as aqueous ammonium acetate, and an eluting solvent, such as acetonitrile.

A method to separate a sample of analytes is provided. A sample of analytes is introduced in a sample solution through a separation column 11. Analytes includes neutral species, such as polycyclic aromatic hydrocarbons, alkyl benzenes, alkyl phenyl ketones, and steroids, and charged species, such as peptides. The sample solution may comprise a buffer, such as aqueous ammonium acetate, and an eluting solvent, such as acetonitrile.

The separation column 11 includes a separation channel 13 and a fritless, homogeneous separation medium 15 in the channel 13. The separation column 11 may be a capillary or planar structure. The separation medium 15 preferably does not have frits or chromatographic particles. The use of a homogeneous separation medium is advantageous because, in some applications, the use of chromatographic particles (i.e., inhomogeneous separation phase) introduces unwanted broadening (i.e., lack of resolution). The separation medium 15 may possibly include two sections containing substantially the same porous homogeneous stationary phase, and the two sections may be separated by another section, such as a monolith with a different pore size or surface charge. Preferably, the separation medium 15 is continuous.

The separation medium 15 includes a metal organic photopolymer and concentrates the analytes on the column. The sample may be introduced by applying a pressure or a voltage to the column 11. For example, the pressure may be 0.5 psi or 20 psi for a period of time, such as two to 1920 seconds, or a field strength of about 40 V/cm may be applied for a period of time. For example, an injection plug length of greater than about two centimeters may be injected into the column 11.

The analyte is concentrated by the column 11. The extent of preconcentration is purely dependent on the retention factor, the k value. The retention factor is affected by the nature of the solvent, the nature of the analyte, and the detailed morphology of the separation medium. Moreover, the flow rate hardly influenced the extent of preconcentration.

The highly porous nature of the porous matrix results in a high mass transfer rate for the analyte, which facilitates the preconcentration effect. The high mass transfer rates arise from the enhanced accessibility of the analytes to the binding sites of the porous structure. Because of the high mass transfer rates, the kinetics of analyte-porous matrix interaction (i.e., the partitioning of the analyte between the mobile and stationary phases) is not the rate-limiting step in the separation. The high mass transfer rate distinguishes this separation method from previous forms of chromatographic separations. With this separation method, because of the high mass transfer rate, it is possible to inject and concentrate larger volumes of sample solution than in columns containing normal chromatographic materials.

The total preconcentration effect is directly proportional to the retention factor, with longer injection plug lengths (e.g., greater than about 25 mm) leading to severe peak broadening of analytes having low-k values. This behavior implies a maximum length of sample plug for each analyte before peak shape becomes compromised.

A major advantage of on-line preconcentration is that it lowers the detection limit for a given analyte. Another advantage is that preconcentration may be used to clean up the analytes from possible interfering species found in the sample matrix.

A separation solution is caused to flow through the column 11, thereby separating and eluting the analytes. The separation solution may be caused to flow by applying a voltage or a pressure to the column 11. For example, the pressure may be 0.5 psi or 20 psi for a period of time, such as two to 1920 seconds, or a field strength of 300 V/cm may be applied for a period of time. The separation solution may comprise a buffer, such as aqueous ammonium acetate, and an eluting solvent, such as acetonitrile. In one embodiment, the separation solution is the same as the sample solution.

The porous matrix acts to extract the analytes from solution as well as provides the stationary phase for chromatographic separation of the analytes. It is this extractor-separator combination that gives this method such power. For example, more than about two-centimeter plugs of sample solution can be loaded into the capillary and concentrated using a separation solution that is the same as the sample solution.

In one embodiment, in addition to the effect exerted by the porous matrix a solvent gradient may be used to further enhance preconcentration of the analytes. In this embodiment, the sample may be dissolved in a solution with a higher concentration of a buffer (e.g., water) than in the separation solution. The higher concentration of the buffer in the sample solution increases the affinity of the sample to the stationary phase. When a solvent gradient is used, the plug length can be longer than the length of the column. For example, injection of a 91.2-cm plug, which was more than three times the total length of the capillary, was possible with only a minor loss in resolution. Improvements in peak heights obtained under gradient conditions can be more than a thousand-fold.

For neutral analytes, two approaches exist for using gradients on the porous matrix. The first approach is to increase the organic solvent ratio between the separation solution and the sample solution. The second approach is to increase the retention factor k in the separation by increasing the percentage of water in the separation solution while maintaining a reasonable percentage of organic solvent between the separation solution and the sample solution. Analysis is faster with the first approach, whereas the resolution is better with the second one.

In another embodiment of the present invention, in addition to the effect exerted by the porous matrix, sample stacking may be used to further enhance the preconcentration of analytes. Sample stacking is the focusing of charged analytes when analytes pass the concentration boundary that separates regions of high and low electric field strengths. The high electric field zone is a lower conductivity sample solution containing more of the eluting solvent, whereas the low electric field region is a higher conductivity separation solution. The eluting solvent, such as acetonitrile, has a lower conductivity than the buffer, such as aqueous ammonium acetate. Thus, a higher concentration of the eluting solvent results in lowering the sample matrix conductivity.

The separation column is prepared with the separation solution. When analytes are introduced into the separation column and a voltage is applied, the analytes in the sample solution at the inlet of the column rapidly accelerate toward the separation solution (lower electric field strength) already in the column, where on crossing the boundary between the sample solution and the separation solution, they slow down and stack into narrow zones at the interface.

Sample stacking is basically caused by the change in electrophoretic velocity at the concentration boundary. Electrophoretic velocity is the product of electrophoretic mobility and electric field strength. Focusing occurs (sample stacking) when the electrophoretic velocity decreases at the concentration boundary. Sample stacking is also explained using the fundamentals of isotachophoresis and Kohlrausch rules.

There are two approaches to perform sample stacking on a porous matrix. The first approach is to increase the percentage of organic solvent, such as acetonitrile. The second is to decrease the concentration of the buffer component in the sample solution. Increasing the percentage of acetonitrile or other suitable organic solvent is especially useful for real samples containing high concentration of salts. Desalting, for example by dialysis, is therefore not necessary to make a lower conductivity solution for injection. Use of organic solvents is also usefull for biological samples when deproteination is part of the sample preparation.

The invention is described in more detail by the way of the following examples. The following examples are presented solely for the purpose of further illustrating and disclosing the present invention, and are not to be construed as limiting the invention.

EXAMPLE 1

Materials and Chemicals. Fused-silica capillaries (75-μm i.d.×365-μm o.d.) were purchased from Polymicro Technologies, Phoenix, Ariz. Methacryloxypropyltrimetoxysilane (MPTMS) was purchased from Gelest, Tullytown, Pa. and Sigma-Aldrich, Milwaukee, Wis. and was used without purification. HPLC-grade toluene, phenanthrene, pyrene, alkyl benzenes, alkyl phenyl ketones, and steroids were purchased from Sigma-Aldrich, Milwaukee, Wis. Irgacure 1800 was received from Ciba, Tarrytown, N.Y.

Instrumentation. A Beckman P/ACE 2000 capillary electrophoresis instrument with a UV-absorbance detector was used to carry out all CEC experiments. An XL-1500 UV cross-linker, available from Spectronics Corp., Westbury, N.Y., equipped with six 15 W blacklight tubes of predominantly 365-nm wavelength was used to irradiate the reaction solutions. Scanning electron microscopy (SEM) analyses were performed on a Philips SEM 505 scanning electron microscope, available from Eindhoven, Netherlands.

Polymerization Procedure. The monomer stock solution was prepared just prior to use by adding 375 μL of MPTMS to 100 μL of 0.12 N HCl. This solution was stirred at room temperature for approximately thirty minutes to afford a clear, monophasic solution. An appropriate amount of toluene (porogen) was added to the monomer stock solution, as shown below in Table 1.

TABLE 1

| Capillary Column | % toluene (v/v) |
| --- | --- |
| A | 90 |
| B | 80 |
| C | 75 |
| D | 73 |
| E | 65 |
| F | 50 |

The photoinitator, Irgacure 1800, was added first to the toluene as 5% of the total weight of the toluene/monomer stock solution. This photoinitator solution was then added to the corresponding amount of monomer stock solution, and stirred for thirty minutes at room temperature to afford a yellow, moniophasic solution. To minimize the evaporation of toluene, the solution was prepared in a vial with a polysilicone cap through which the capillary was inserted during filling with the solution.

A 15-cm stripe of the polyimide coating on a 30-cm long capillary was removed using a razor blade positioned at 45° to the capillary surface. The mechanical stability of the capillary was remarkably good despite the removal of a stripe of polyimide coating. The irradiation light entered the capillary only through this 15-cm stripe. No monolith was formed in the capillary where the polyimide coating ("mask") remained intact.

Using a 0.5-mL disposable syringe, approximately 0.2 mL of the reaction solution was flushed through the capillary to wet thoroughly the wall surface before filling the capillary with the solution. This resulted in bonding of the monolith to the capillary wall. No special pretreatment of the capillary wall was necessary to bonds the monolith to the wall. The filled capillaries were irradiated (900 mJ/cm$^2$) in a UV cross-linker using 365-nm light for five minutes to form the porous matrix.

After irradiation, the capillaries were washed with ethanol using a hand-held syringe to removed unreacted reagents or porogens. Because the monoliths were highly permeable, high pressures were not required to drive liquid through the capillaries. Once the unreacted reagents were removed, the monolith became opaque and could be viewed clearly through the capillary without the aid of a microscope. The homogenity of the porous matrix was confirmed at 100× magnification. Burning off the polyimide coating immediately after the monolith section with fuming sulfuric acid made a detection window.

Once fabricated, the capillary was successfully installed in the cartridge without any damage. The capillary was conditioned with the separation buffer for approximately five minutes using a syringe and a band-held vise. Once in the instrument, the capillary was further conditioned by pressure rinsing (20 psi) with the separation buffer or by electrokinetically conditioning at 5 kV or 10 kV for thirty minutes.

Characterization. SEM was used to study the morphology of the separation column. A capillary was sectioned carefully to expose the monolith. The sectioned pieces of capillary were sputtered with gold prior to SEM analyses.

Analyte Separation. The analytes were prepared in the mobile phase to prevent gradient effects during the CEC experiments. The mobile phase was made up of various ratios (v/v) of 50 mM ammonium acetate, water, and acetonitrile. A new sample solution was used for every injection to maintain the same concentration of acetonitrile in the sample solution and the mobile phase.

FIG. 2A is a representative electrochromatogram showing a plot of absorbance versus retention time for column B. The separation was performed with a 50 mM ammonium acetate/water/acetonitrile (1/3/6) solution. The sample solution was injected at 0.5 psi pressure for three seconds, and the separation was performed with an applied voltage of 1 kV at a temperature of 20° C. and detected at 214 nm. The elution order of the separation was (1) thiourea, (2) tetrahydrofuran, (3) naphthalene, (4) phenanthrene, (5) fluoranthene, (6) pyrene, (7) 1,2-benzanthracene, and (8) 1,2,5,6-bienzanthracene.

FIG. 2B is a representative electrochromatogram showing a plot of absorbance versus retention time for column D. The separation was performed with a 50 mM ammonium acetate/ water/acetonitrile (1/4/5) solution. The sample solution was injected at 0.5 psi pressure for three seconds, and the separation was performed with an applied voltage of 15 kV at a temperature of 20° C. and detected at 200 nm. The elution order of the separation was (1) benzene, (2) toluene, (3) ethylene benzene, (4) propyl benzene, (5) butyl benzene, and (6) hexyl benzene.

The elution order of the column was similar to that of reversed-phase chromatography with the larger molecular weight or more hydrophobic analytes eluting later than the smaller molecular weight or more hydrophilic analytes. Elution of the analytes in both figures occurred in less than seven minutes. Bubble formation was not a problem during the CEC experiments, for which the typical operating currents were between 3 and 10 $\mu$A.

For a typical capillary column D, efficiencies of up to 100,000 plates/m are achieved for thiourea, a less-retained compound. Small variations in the elution times were observed for thiourea (0.65% RSD), naphthalene (1.10% RSD), phenanthrene (1.14% RSD), and pyrene (1.14% RSD) over a period of three days (n=33).

FIG. 3 is a representative electrochromatogram showing a plot of absorbance versus retention time for column D. The separation was performed with a 50 mM ammonium acetate/ water/acetonitrile (1/3/6) solution. The sample solution was injected at 0.5 psi pressure for three seconds, and the separation was performed with an applied voltage of 1 kV at a temperature of 20° C. and detected at 214 nm. A sample of thiourea, napthalene, phenanthrene, and pyrene was separated within 110 minutes at an applied pressure of only 20 psi (the maximum limit of the instrument). Peak tailing was most severe for pyrene because of its strong interaction with the porous matrix, and tailing was not observed for thiourea, which has low retention on the column.

FIG. 4A is a scanning electron micrograph of the cross-section of a metal organic photopolymer formed with 80% (v/v) toluene (capillary B) in a 75-$\mu$m-i.d. capillary column. The micrograph showed an interconnecting network of 1-$\mu$m spherical structures through which micrometer-sized macropores (as large as 5 $\mu$m) are interspersed.

FIG. 4B is a scanning electron micrograph of the cross-section of a metal organic photopolymer formed with 50% (v/v) toluene in a 75-$\mu$m-i.d. capillary column. In contrast to the porous matrix shown in FIG. 4A, the structure shown in FIG. 4B was a dense photopolymer with macropores of 2 $\mu$m or less in diameter. Consequently, the matrix in FIG. 4B was less permeable, and a significant back pressure occurs. No liquid could be driven through the column at pressures near 200 psi.

The permeability of a porous matrix was determined by the linear velocity of the porous matrix, which is proportional to permeability as described in Darcy's law. The permeability of a porous matrix as a function of the macropore size was highly dependent on the volume and type of porogen used to prepare the photopolymer. For a column made with 90% (v/v) toluene (column A), the linear velocity is 12.3 cm/min, and an 80% (v/v) column (column B) had a linear velocity of 3.3 cm/min, whereas a column made with 73% (v/v) toluene (column D) had a linear velocity of 0.6 cm/min. These linear velocity data suggested that the macropores decrease with decreasing porogen concentration. This behavior was consistent with what has reported in the literature.

EXAMPLE 2

The separation column was prepared as described in Example 1. A mixture of 1:1 hexane/toluene was used for the porogen. The separation column had a separation performance similar to that of a separation column made with 80/20 toluene/reaction solution. A column efficiency of 68,000 plates/m (RSD 7.0%, n=5) for thiourea and an electroosmotic flow (EOF) velocity of 3.7 cm/min was obtained.

EXAMPLE 3

A mixture of 375 $\mu$L of MPTMS and 100 $\mu$L of 0.12 M hydrochloric acid was stirred for thirty minutes at room temperature. 27 parts of this mixture were combined with 73 parts of toluene to give 200 $\mu$L of the final solution. 5% by weight of the final solution of the photoinitator Irgacure 1800 was added, and the resulting sol-gel solution was stirred for five minutes before use. A 75-$\mu$m i.d.×365-$\mu$m o.d. fused silica capillary was filled with the sol-gel solution, and the separation column was exposed to UV light in a Spectrolinker Xl-1500 at 365 nm to affect photopolymerization. The polymerization length of the porous matrix was controlled by removing a 15-cm strip of the polyimide coating of the capillary prior to irradiation for five minutes. Unreacted reagents were flushed with ethanol. The total length of the capillary was 25.6 cm (18.8 cm from inlet to the detector window). The resulting column was conditioned with the separation solution prior to use.

All electrophoresis experiments were performed with a Beckman P/ACE 2000. The capillaries were thermostated at 20° C. Injections were done using pressure (i.e., 0.5 psi and 20 psi) or voltage (1 kV to 10 kV) and varied in duration from two seconds to 1920 seconds. Detection was done at 214 or 254 nm. Data analysis was performed with GRAMS/ 32 version 4.02, available from Galactic Industries Corporation, Salem, N.H.

FIGS. 5A and 5B are representative electrochromatograms showing plots of absorbance versus retention time using an embodiment of the present invention. The figures illustrate the increase in detection sensitivity with an increase in injected plug length in the CEC separation of a mixture containing the small molecule, thiourea, three polycyclic aromatic hydrocarbons (PAHs), and eight alkyl phenyl ketones. To eliminate solvent gradient effects, the sample was prepared in the separation solution. The sample and separation solutions were 50 mM ammonium acetate/water/ acetonitrile (1/4/5). In FIG. 5A, the plug lengths were 0.1 mm, 6.8 mm, 13.7 mm, 27.4 mm, and 34.2 mm. The 0.1 mm plug length was for an applied pressure of 0.5 psi, whereas all other plug lengths were for an applied pressure of 20 psi. The applied voltage for the separation was 20 kV, and the absorbance was measured at 214 nm. The elution order of the column was (1) 12.5. $\mu$M thiourea, (2) 51.0 $\mu$M naphthalene, (3) 1.0 $\mu$M phenanthrene, and (4) 123 $\mu$M pyrene.

In FIG. 5B, the column was prepared in the same manner as the column as described earlier, except that the column was post-modified by continuous flow of (3,3,3-trifluoropropyl)trichlorosilane for thirty minutes at room temperature and followed by rinsing with toluene. The plug lengths were 0.7 m, 7.2 mm, 10.7 mm, 17.9 mm, and 28.6 mm. The applied voltage was 15 kV, and the absorbance was measured at 254 nm. The elution order of the column was (1) 5 $\mu$M thiourea, (2) acetophenone, (3) propiophenone, (4) butyrophenone, (5) valerophenone, (6) hexanophenone, (7) heptanophenone; (8) octanophenone, and (9) decanophenone. The concentration of each of the alkyl phenyl ketones was 0.1 $\mu$g/mL in the separation solution.

For the PAH mixture illustrated in FIG. 5A, the peaks were barely visible with the typical injection of a 0.1 mm plug length, but the peak heights increased when the plug length increased from 6.8 to 34.2 mm. Thus, the separation column, an embodiment of the present invention, allowed for the injection of a longer plug length than a typical separation column does. Similarly, for the alkyl phenyl ketone mixture illustrated in FIG. 5B, the peak heights increased when the plug length was increased from 0.7 mm to 57.3 mm. As the plug length was increased, all four peaks showed increased broadening, but the later eluting peaks are more symmetrical to a small extent than the earlier ones. This behavior is backwards from what is observed in typical chromatographic separations in which the later eluting peaks are less symmetrical than the earlier ones because of dispersion effects. These results suggest that the analytes accumulate at the inlet of the poroux matrix during the injection, with the more retentive species being localized more effectively than the less retentive ones.

In FIG. 5A, the improvement in peak heights for a 27.4-mm injection compared to a typical injection of 0.1 mm is 50, 125, and 127 times for naphthalene, phenanthrene, and pyrene, respectively. The sample solution in the 27.4-mm injection is a 10-fold dilution of the sample in the typical 0.1-mm injection.

EXAMPLE 4

The separation column was prepared as described in Example 3. The sample and separation solution was 50 mM ammonium acetate/water/acetonitrile (1/3/6). The samples were injected at 1 kV. The applied voltage was 15 kV, and the absorbance was detected at 214 nm. FIG. 6 is a representative electrochromatogram of a plot showing absorbance versus retention time using an embodiment of the present invention. 39.0 mM of naphthalene in the separation solution was injected for five seconds, as represented by signal a, and a 3.9 mM of naphthalene in the separation solution was injected for eighty-five seconds, as represented by signal b. The corrected peak areas (peak area/migration time) for both electrochromatograms were made close to each other by controlling the injection time of the ten-fold dilution of sample. The corrected peak areas of the electropherogram in lines a and b are 0.0023 (%RSD=0.02%, n=3) and 0.0025 (%RSD=0.00, n=3) arbitrary units/min, respectively. This comparison was done such that the amount of naphthalene molecules injected for each run is the same.

Preconcentration was evidenced by the slightly higher peak height for the longer injection of diluted sample and almost the same corrected peak widths (peak width/migration time) for both experiments, despite the different sample concentration. The peak heights of the electrochromatograms in signals a and b were 0.0869 (%RSD=0.36%, n=3) and 0.0937 (%RSD=0.06%, n=3) arbitrary units, respectively. The peak widths of the electrochromatograms in signals a and b were 0.0253 (%RSD=0.07%, n=3) and 0.0249 (%RSD=0.01%, n=3) arbitrary units/min, respectively. The shift in migration time on line b was caused by the longer injection time, which made the center of the sample plug closer to the detector window.

EXAMPLE 5

A mixture of 575 $\mu$L of MPTMS and 100 $\mu$L of 0.12 M hydrochloric acid was stirred for thirty minutes at room temperature. 20 parts of this mixture were combined with 80 parts of toluene to give 200 $\mu$L of the final solution. The photoinitiator was added as 10% of the total volume of the final solution, and the resulting sol-gel solution was stirred for five minutes before use. The separation column was prepared as described above in Example 3. Unreacted reagents were flushed with toluene. The surface of the porous matrix was modified by continuous flow of pentafluorophenyltrichlorosilane through the capillary for forty-five minutes at room temperature and followed by rinsing with toluene.

FIG. 7 (panels a and b) are representative electrochromatograms showing plots of absorbance versus retention time using an embodiment of the present invention. The separation solution was 50 mM phosphoric acid/water/acetonitrile (1/5/4). The applied voltage was 15 kV, and the absorbance was detected at 214 nm. FIG. 7 (panel a) shows a 0.5 psi injection at 0.1 mm plug length of test peptides, and FIG. 7 (panel b) shows a 0.5 psi injection at 12 mm plug length of test peptides. The test peptides, which were charged analytes, were (1) bradykinin, (2) angiotensin II, (3) tripeptide I, (4) tripeptide II, and (5) methionine enkephalin. The concentration of the peptides were 16.7 $\mu$g/ml. The cathode directed velocities of the peptides were dictated by both electrophoretic and electroosmotic flow effects. The peptides had a net positive charge at the pH of the separation solution (pH=2). The improvement in peak heights for the longer injection compared to a typical injection of 0.1 mm plug length is 21, 19, 16, 18, and 22 times for bradykinin, angiotensis II, tripeptide I, tripeptide II, and methionine enkephalin, respectively. This result demonstrates the usefulness of this method for charged analytes.

EXAMPLE 6

The separation column was prepared as in Example 3. FIG. 8 (panels a, b, and c) are representative electrochromatograms showing plots of absorbance versus retention time using an embodiment of the present invention. FIG. 8 shows an analysis of a urine sample, spiked with 0.1 mM hydrocortisone (peak 1), 0.3 mM progesterone (peak 2) and 0.2 mM cortisone (peak 3). Four parts of spike or unspiked urine were mixed with six parts of acetonitrile and centrifuged to remove proteins. One part of each supernatant was mixed with one part of 50 mM ammonium acetate/water/acetonitrile (1/7/2) before injection. FIG. 8 (panel a) shows an injection plug length of 0.1 mm, and FIG. 8 (panel b) shows an injection plug length of 21.4 mm. FIG. 8 (panel c) represents a 21.4-mm injection plug length of urine blank. The separation solution consisted of 50 mM ammonium acetate/water/acetonitrile (1/5/4). The applied voltage for the separation was 17 kV, and the absorbance was measured at 254 nm. After protein precipitation with acetonitrile, these steroids were detected and quantified with a 21.4-mm injection of the sample solution, but are weakly detected with a typical 0.1-mm injection. A comparison between the blank run and the spiked run showed that the sample matrix, which still contained other biomolecules, did not significantly interfere with steroid analysis on the separation column. This result demonstrates the usefulness of the technique for biofluid analysis.

EXAMPLE 7

The separation column was prepared as described in Example 3. FIG. 9 (panels a, b, c, d, and e) are representative electrochromatograms showing plots of absorbance versus retention time using an embodiment of the present invention. Sample plug lengths of 1.1 cm were injected. The separation solution was 5 mM ammonium acetate in 60% acetonitrile, and the sample solutions were 5 mM ammonium acetate in 60% acetonitrile (panel a), 50% acetonitrile (panel b), 40% acetonitrile (panel c), 30% acetonitrile (panel d), and 20% acetonitrile (panel e). The applied voltage for the separation was 15 kV, and the absorbance was detected at 254 nm. The elution order was (1) thiourea, (2) acetophenone, (3) propiophenone, (4) butyrophenone, (5) valerophenone, (6) hexanophenone, (7) heptanophenone, (8) octanophenone, and (9) decanophenone. The concentration of each analyte was 2 nl/ml.

The retention factors, k, obtained for acetophenone (peak 2), propiophenone peak 3), butyrophenone (peak 4), valerophenone (peak 5), hexanophenone (peak 6), heptanophenone (peak 7), octanophenone (peak 8), and decanophenone (peak 9) were 0.18, 0.25, 0.32, 0.41, 0.53, 0.67, 0.85, and 1.33, respectively. In this study, thiourea (peak 1) was used as the essentially unretained neutral solute for the determination of k. The value of k and migration time follows the increase in alkyl chain length. In general, the peak shapes and resolution improved when the water concentration was increased from 40% to 50%, 60%, 70%, and 80%, as evidenced by panels a, b, c, d, and e, respectively.

EXAMPLE 8

The experimentation conditions were the same as in Example 7. FIG. 10 is a graphical representation of a plot showing the logarithm of peak height ratio (peak height obtained from a higher concentration of water in the sample matrix divided by peak height obtained from a sample matrix similar to that of the separation solution) versus the percentage of water in the sample matrix. The data indicated that a limit exists to which the peak heights can be improved by increasing the concentration of the buffer in the sample matrix. Preconcentration was improved owing to the increased attraction of the analytes to the porous matrix. When the value for the logarithm of the peak height ratio was less than 1, about 1, or greater than 1 there was a decrease, no change, or increase, respectively, in peak height compared to a similar injection using the separation solution as the sample matrix. For all test APKs, peak heights improved when the water concentration was increased from 40% to 50% and from 50% to 60%. Peak heights did not improve when the percentage of water was increased from 60% to 70% or more, except for the two lowest k analytes (acetophenone and propiophenone) when the percentage of water was increased from 60% to 70%. Peak heights worsened for the higher k analytes (heptanophenone, octanophenone, and decanophenone) in the 80% water matrix. The reason for the decrease in peak heights is the decrease in the solubility of the high k analytes in the highly aqueous sample matrix. The corrected peak areas, which is a measure of the amount of sample loaded for octanophenone and decanophenone is 10% to 60% lower in the 80% water matrix compared to the other sample matrices used. To avoid solubility problems, the test APKs in succeeding experiments were prepared in matrices having at least 30% acetonitrile.

EXAMPLE 9

The separation column was prepared as described above in Example 3. FIG. 11 (panels a, b, and c) are representative electrochromatograms showing plots of absorbance versus retention time using an embodiment of the present invention. The separation solution is 5 mM ammonium acetate in 60% acetonitrile. The plug lengths were 0.2 cm for a sample solution of 5 mM ammonium acetate in 60% acetonitrile (panel a); 2.74 cm for the same sample solution was used in panel a (panel b), and 2.74 cm for a sample solution of 5 mM ammonium acetate in 30% acetonitrile (panel c). Other conditions and identification of peaks are the same as in Example 7.

The gradient condition, as shown in FIG. 11 (panel c), showed improved resolution and peak shapes. Improvements in peak heights under the gradient condition illustrated in FIG. 11 (panel c) were 36, 35, 38, 41, 42, 38, 32, and 24 times for acetophenone, propiophenone, butyrophenone, valerophenone, hexanophenone, heptanophenone, octanophenone, and decanophenone, respectively. The %RSDs (n=5) of measured peak heights ranged from 0.9% to 2.5%. %RSDs (n=5) of migration time ranged from 0.3% to 0.5%. The procedure is therefore reproducible in a single column

EXAMPLE 10

FIGS. 12A, 12B, and 12C are representative electrochromatograms showing plots of absorbance versus retention time using an embodiment of the present invention. The plug lengths were 2.74 cm for sample solution of 5 mM ammonium acetate in 40% acetonitrile (FIG. 12A), 2.74-cm for sample solution of 5 mM ammonium acetate in 30% acetonitrile (FIG. 12B), and 5.48 cm for a sample solution the same as in FIG. 12B (FIG. 12C). The separation solutions were 5 mM ammonium acetate in 60% acetonitrile (FIG. 12A) and 5 mM ammonium acetate in 50% acetonitrile (FIGS. 12B and 12C). Other conditions and identification of peaks are the same as in Example 7.

The kvalues were higher in FIG. 12B than in FIG. 12A because of the high percentage of water in the separation solution. The analyte molecules were more attracted to the PSG phase at high percentages of water. The distribution constant K (number of moles of solute in the PSG phase divided by the number of moles of solute in the separation solution), which is directly proportional to k increases with increasing concentration of water in the separation solution. In FIG. 12B, the k values for acetophenone, propiophenone, butyrophenone, valerophenone, hexanophenone, heptanophenone, octanophenone, and decanophenone were 0.29, 0.47, 0.65, 0.92, 1.28, 1.76, 2.37, and 4.25, respectively. To maintain the gradient effect constant, the percentage of organic solvent ratio between the separation solution and sample matrix was kept at the same value for FIGS. 12A and 12B. For reasons still unknown, the result in FIG. 12B shows that for analytes with lower k values (acetophenone and propiophenone) there were slight increases in peak heights compared to FIG. 12A. For the other test solutes, there are some decreases in peak heights.

FIG. 12C illustrates what happens for a longer injection plug of 5.48 cm and a higher percentage of water in the separation solution. Improvements in peak heights were 31, 33, 55, 44, 44, 37, 29, and 19 times for acetophenone, propiophenone, butyrophenone, valerophenone, hexanophenone, heptanophenone, octanophenone, and decanophenone, respectively. As in FIG. 11 (panel c), the improvements in peak heights do not follow k, unlike in nongradient conditions. The improvements in peak heights were comparable to those obtained with a higher percentage of organic solvent between the separation solution and the sample matrix (FIG. 11, panel c). Note that the injection plug is two times shorter in FIG. 11 (panel c) than in FIG. 12C.

EXAMPLE 11

FIG. 13 (panels a and b) are representative electrochromatograms showing plots of absorbance versus retention time using an embodiment of the present invention. The plug lengths were 0.22 mm (panel a) and 19.5 cm (panel b). The separation solution was 5 mM ammonium acetate in 60% acetonitrile. The sample solutions were: 5 mM ammonium acetate in 60% acetonitrile (panel a) and 36% acetonitrile (panel b). The sample concentrations were 11 to 53 µg/ml (panel a) and 1.1 to 5.3 µg/ml (panel b). The applied voltage was 30 kV, and the absorbance was detected at 214 nm. The elution order was thiourea (peak 1), naphthalene (peak 2), phenanthrene (peak 3), pyrene (peak 4), and benz(e) acephenanthylene (peak 5).

A solvent gradient improved detection of four PAHs, as shown in FIG. 13 (panel b). A high percentage of acetonitrile (60%) in the separation solution, a shorter PSG length (10 cm), and a high electric-field strength (781.3 V/cm) were used for faster analysis times. FIG. 13 (panel a) is a 0.22-mm typical injection of sample prepared in the separation solution. FIG. 13 (panel b) is a 19.5-cm injection using a gradient where the sample is in a 36% acetonitrile matrix, which provides a high percentage of organic solvent between the sample solution and the separation solution. Longer than 19.5-cm plug lengths cause broadering of the naphthalene peak. It is interesting to note that the injection length is longer than the length from the inlet to the detector window (18.8-cm). The faster eluting thiourea zone is actually observed during the sample injection. The thiourea zone is therefore at the detection window at the start of the separation voltage.

Improvements in peak heights for naphthalene (peak 2), phenanthrene (peak 3), pyrene (peak 4), and benz(e) acephenanthylene (peak 5) are 346, 437, 409, and 315 times, respectively. The sample concentrations in FIG. 13 (panel b) were 10-fold lower than in FIG. 13 (panel a). For naphthalene, phenanthrene, and pyrene, the values stated above are 6.9, 3.5, and 3.2 times better than that previously reported under nongradient conditions, respectively.

EXAMPLE 12

FIG. 14 (panels a, b, c, d, and e) are representative electrochromatograms showing plots of absorbance versus retention time using an embodiment of the present invention. The plug lengths were 0.23 mm (panel a), 7.6 cm (panel b), 22.8 cm (panel c), 45.6 cm (panel d), and 91.2 cm (panel e). The separation solution was 5 mM ammonium acetate in 60% acetonitrile. The sample solutions were: 5 mM ammonium acetate in 60% acetonitrile (panel a) and 40% acetonitrile (panels b, c, d, and e). The sample concentrations were 9 to 50 µg/ml (panel a), 0.9 to 5 µg/ml (panels b, c, d, and e). The applied voltage was 22 kV, and absorbance was detected at 254 nm. The elution order was thiourea (peak 1), decanophenone (peak 2), and pyrene (peak 3).

The peak heights of decanophenone (peak 2) and pyrene (peak 3) increased with increasing plug lengths. The injection was increased from 0.23 mm (panel a) to 7.6 cm (panel b), 22.8 cm (panel c), 45.6 cm (panel d), and 91.2 cm (panel e), which corresponds to 0.1%, 30%, 89%, 178%, and 356% of the total capillary length. The high porosity or the low resistance to flow of the porous matrix made it possible to introduce increasing lengths of the sample solution in a rather effortless manner. Longer than 91.2 cm injection is still possible. It is not performed, however, owing to loss of resolution as observed in FIG. 14 (panel e). The electrochromatogram in panel d or e is believed to be the first demonstration in CEC showing sample injections longer than the total capillary length. The volume of sample injected was also greater than 1 µl. A comparison of the peak heights obtained in panels a and e suggests improvements in peak heights of 1118 times and 1104 times for decanophenone and pyrene, respectively. These values are the highest reported sensitivity improvements for neutral analytes using a simple on-line preconcentration technique in CEC. The strong interaction of the analytes to the porous matrix and the inherent rapid mass transfer characteristics of the porous matrix allowed for the observation of such marked preconcentration effects.

Successful separations have been done with PSG in 250-µm i.d. capillaries (data not shown). This work opens the possibility of performing semi-preparative separations involving long plug injections. Injection volumes in the µl range could easily be made.

EXAMPLE 13

FIG. 15 (panels a, b, c, d, e, and f) are representative electrochromatograms showing plots of absorbance versus retention time using an embodiment of the present invention. The plug lengths were 0.1 mm (panel a) and 1.8 cm (panels b, c, d, e, and f). Injections were done using pressure wherein the injection length is fixed at 1.8 cm. The sample solutions were the same as the separation solution (panels a and b), 10 mM phosphoric acid in 20% acetonitrile (panel c), 10 mM phosphoric acid in 70% acetonitrile (panel d), 50 mM phosphoric acid in 40% acetonitrile (panel e), 0.05 mM phosphoric acid in 40% acetonitrile (panel f). The separation solution was 10 mM phosphoric acid in 40% acetonitrile. The peptide concentrations were 16.7 µg/ml each, the applied voltage was 12 kV, and the absorption detection was at 214 nm. The elution order was bradykinin (peak 1), angiotensin II (peak 2), tripeptide I (peak 3), tripeptide II (peak 4), and methionine enkephalin (peak 5).

Although it was expected that the peak shapes would be better under a gradient condition (FIG. 15, panel c) as compared to a nongradient one (FIG. 15, panel b), the resulting peak shapes were better using a higher concentration of acetonitrile in the sample matrix (FIG. 15, panel d). Better peak shapes were observed in FIG. 15 (panel d) resulting from sample stacking. The broadening effect of using a higher concentration of the eluting solvent in the sample solution (reverse gradient effect due to higher concentration of eluting solvent) is not observed because the cationic peptides immediately migrate to the separation buffer once voltage is applied, thus the peptide zones are already in the separation solution before it reaches the porous matrix. Sample stacking is also shown in FIG. 15 (panel f) where the sample is prepared in a matrix having a lower concentration of buffer component and a similar percentage of acetonitrile compared to the separation solution.

Undesirable peak shapes are observed in FIG. 15 (panel c) resulting from destacking. Destacking is the broadening of charged analytes when analytes pass the concentration boundary that separates regions of low and high electric field strengths. The low electric field zone is the high conductivity sample matrix containing more water. Destacking is also shown in FIG. 15 (panel e) where the sample is prepared in a matrix having a higher concentration of buffer component and a similar percentage of acetonitrile compared to the separation solution.

EXAMPLE 14

FIG. 16 (panels a and b) are representative electrochromatograms showing plots of absorbance versus retention time using an embodiment of the present invention. The injections were 0.1 mm using 0.5 psi pressure (panel a) and 15-s at 5 kV (panel b). The sample solutions were 10 mM phosphoric acid in 40% acetonitrile (panel a) and 0.5 µM phosphoric acid in 40% acetonitrile (panel b). The peptide concentrations were 16.7 μg/ml each (panel a) and 167 ng/ml each (panel b). The separation voltage was 12 kV. Other conditions are the same as in Example 13.

The analytes in FIG. 16 (panel b) were one hundred times less concentrated than those in FIG. 16 (panel a). Improvements in peak heights for bradykinin (peak 1), angiotensin II (peak 2), tripeptide I (peak 3), tripeptide II (peak 4), and methionine enkephalin (peak 5) were 1040, 820, 810, 950, and 711 times, respectively. For the preconcentration procedure, %RSDs (n=5) of peak heights ranged from 6.2% to 16.2% while %RSDs (n=5) of migration time ranged from 0.7% to 1.5%. Reproducibility of peak heights should be improved with the use of an internal standard.

Field enhanced sample injection was performed by dissolving the sample in a low conductivity matrix (0.5 μM phosphoric acid in 40% acetonitrile), followed by injection using voltage with the negative electrode at the detector end. As the voltage was applied, the low conductivity sample matrix entered the capillary by virtue of electroosmotic flow (EOF) while the cationic peptides entered the column by virtue of both EOF and electrophoretic flow. Only a very small plug of sample matrix was introduced because the low pH of the separation solution markedly decreases the EOF, which prevents the dissociation of silanol groups at the capillary walls. An unretained neutral solute (thiourea) was actually detected after 30 minutes.

The electric field in the sample matrix zone introduced into the column was much higher than the separation zone. This effect caused the high electrophoretic velocity of the cationic peptides entering the capillary. The high analyte electrophoretic velocity caused a large amount of peptides to be introduced, unlike in hydrodynamic injection, the volume of sample loaded limited the amount of sample introduced. The high analyte electrophoretic velocity also caused focusing or preconcentration of peptides at the concentration boundary between the sample matrix and separation solution (sample stacking). Introduction of a water plug before electrokinetic injection, which is suggested to be useful in sample stacking with electrokinetic injection, did not improve the peak heights because of the similar direction of the EOF and analyte electrophoretic velocities. The low conductivity sample matrix that entered the capillary also maintained the enhancement of the electric field at the inlet end of the capillary during injection.

With the conditions in FIG. 16, optimum electrokinetic injection time at 5 kV was found to be 15 s. Longer injections lead to broadening of the peaks. After the injection, the separation voltage was applied with the same polarity as in the injection (negative electrode at the detector side). The analytes moved to the cathode and were subsequently preconcentrated again based on their retention on the PSG column. The method was considered selective for cations because cations were mostly introduced into the capillary. The injected neutrals migrated after the unretained neutral marker and the cations because the EOF was very slow. At the pH used, all the analytes were either positively charged or neutral. Applicability of the technique to other cationic samples is also possible.

EXAMPLE 15

Table 2 lists the types and volumes of reagents used to make different precursor stock solutions where the ratio of the acid catalyst to the precursor, methacryloxypropyltriethoxysilane, was varied or where the precursor was reacted with a co-precursor (to form a mixed phase PSG monolith).

TABLE 2

| Solution | Volume (μL) | | | |
| --- | --- | --- | --- | --- |
| | Precursor[1] | BTE[2] | BTO[3] | HCl[4] |
| A | 375 | 0 | 0 | 100 |
| K | 375 | 200 | 0 | 100 |
| J | 575 | 0 | 0 | 100 |
| M | 500 | 0 | 75 | 100 |
| P | 375 | 200 | 0 | 100 |

[1]methacryloxypropyltriethoxysilane
[2]bis(triethoxysilyl)ethane
[3]bis(triethoxysilyl)octane
[4]0.12M Either changing the concentration of the precursor in the reaction solution or using a co-precursor for the formation of mixed phases modified the chemical nature of the parent PSG monolith. The PSG monoliths, PSG-A and PSG-J, prepared from solutions A and J, respectively, differ only in the volume of precursor used in the reaction with J containing a higher volume of the precursor than A. A higher volume of the precursor in the reaction should result in a denser monolith in the capillary column. The PSG monolith, PSG-K, was prepared with the precursor and bis(triethoxysilyl)ethane as a co-precursor. The PSG monoliths, PSG-M and PSG-P, were prepared with the precursor and different amounts of bis(triethoxysilyl)octane as the co-precursor. The co-precursors hydrolyze and condense with the precursor to form hybrid sols (mixed phases).

For solutions A and J, the appropriate volume of the precursor was added to 100 μL of the acid catalyst (0.12 M HCl), and the resulting solution was stirred for 15 minutes at room temperature (in the dark). For solutions K, M, and P, the appropriate volume of the precursor was added to 100 μL of 0.12 M HCl followed by the addition of the appropriate amount of bis(triethoxysilyl)ethane; the resulting solution was stirred for 15 minutes at room temperature (in the dark). All of these solutions were used within two hours of their preparation.

A similar procedure was followed in making the toluene/precursor stock solutions with the photoinitiator added. The amount of photoinitiator added to the toluene/precursor stock solution was 10 mg photoinitiator for every 100 μL of the toluene/precursor stock solution.

The capillary was prepared and conditioned in the same manner as previously described. PSG capillary column conditioning was the same as before.

The separation factors of the monoliths for two test mixtures of alkyl phenyl ketones (APKs) and polycyclic aromatic hydrocarbons (PAHs) were determined. The separation factor is a measure of the analyte separation capability of a chromatographic system. The separation factor, α, is given by $k_2/k_1$, where k is the retention factor for a particular analyte, and $k_2$ and $k_1$ are the k values for adjacent analytes. The retention factor $k=(t_R-t_o)/t_o$ was determined in the usual way, where $t_R$ is the analyte retention time and $t_o$ is the retention time of an unretained marker, for which we used thiourea. Table 3 lists the separation factor of each PSG monolith for naphthalene and pyrene.

TABLE 3

| Monolith | $k_n$ | $k_{Py}$ | $\alpha_{Npy}$ | $R_s(N/Py)$ |
|---|---|---|---|---|
| PSG-A | 0.14 | 0.36 | 2.57 | 2.43 |
| PSG-K | 0.23 | 0.56 | 2.43 | 4.09 |
| PSG-J | 0.31 | 0.79 | 2.55 | 4.35 |
| PSG-M | 0.35 | 0.90 | 2.57 | 4.37 |
| PSG-P | 0.25 | 0.69 | 2.76 | 9.03 |

The values for α varied from 2.43 for PSG-K to 2.76 for PSG-P with the separation factor for PSG-P being slightly higher than that of the other monoliths. Separation factors greater than 1 indicated successful separation of the analytes.

FIG. 17 (panels a, b, c, d, and e) are representative electrochromatograms showing plots of absorbance versus retention time using an embodiment of the present invention. A mixture of thiourea (T), naphthalene (N), phenanthrene (Ph), and pyrene (Py) were separated on PSG-A (FIG. 17, panel a), PSG-K (FIG. 17, panel b), PSG-J (FIG. 17, panel c), PSG-M (FIG. 17, panel d), and PSG-P (FIG. 17, panel e). In all cases the peaks of the different analytes were well resolved.

Resolution was determined from the expression $$R_s = \frac{\sqrt{N}}{4} \frac{(\alpha - 1)}{\alpha} \frac{k}{(k+1)},$$

where N is the efficiency (theoretical plate number), α is the separation factor, and k the retention factor for a particular analyte. PSG-A has the lowest resolution of 2.43 for naphthalene and pyrene whereas PSG-J has a resolution of 4.35 for the same two analytes. The higher volume of the precursor used in the preparation of PSG-J as compared to PSG-A resulted in increased hydrophobicity of the monolith. The retention factors for naphthalene and pyrene on PSG-J were 0.31 and 0.79, respectively, and these values reflected the increase in the hydrophobicity of the monolith. These values represent increases of 55% and 54%, respectively.

The use of the co-precursor, bis(triethoxysilyl)octane in PSG-M and bis(triethoxysilyl)ethane in PSG-K and PSG-P resulted in resolution for naphthalene and pyrene of 4.37, 4.09, and 9.03, respectively, which is an enhancement of up to 73% as compared to the resolution on the parent PSG-A (Rs=2.43). The retention factors for naphthalene (0.23) and pyrene (0.56) were both 60% higher for these three monoliths than for PSG-A.

EXAMPLE 16

The separation column was prepared as described above in Example 15 for monolith PSG-J. For a porous matrix having a length of 15 cm, the retention factors for napthalene and pyrene, $k_N$ and $k_{Py}$, respectively, were 0.31 and 0.79, respectively, for a porous matrix made with 80% toluene. For a similar porous matrix having a length of 10 cm, $k_N$ and $k_{Py}$ were 0.10 and 0.24, respectively. There was a linear relationship between length and $k_N$ (r=0.991) and $k_{Py}$ (r=0.991). The separation factors for 15-cm, 10-cm, and 5-cm porous matrices were 2.55, 2.52, and 2.40, respectively. Thus, for the shortest monolith length, a high separation factor was maintained, while the elution times for the analytes were significantly reduced. Decreasing the length of the porous matrix in a capillary column led to a decrease in the elution times of the test analytes. Decreasing this length had an effect of decreasing the retention factors of naphthalene and pyrene.

EXAMPLE 17

The separation column was prepared as described above in Example 15. For PSG-A made with 80% toluene, $k_N$ was 0.14 and $k_{Py}$ is 0.36, whereas $k_N$ was 0.30 and $k_{Py}$ was 0.74 for PSG-A made with 73% toluene. The separation factors for PSG-A made with 80% toluene and 73% toluene were 2.57 (0.1%RSD) and 2.47 (0.1%RSD), respectively. The value of k increased by 53% and 51% for naphthalene and pyrene when 73% toluene was used in the preparation of the monoliths.

A similar trend was observed for PSG-J where $k_N$ was 0.31 and $k_{Py}$ was 0.79 for a monolith made with 80% toluene. The $k_N$ (0.49) and $k_{Py}$ (1.23) values increased by 37% and 36% when the concentration of toluene was decreased from 80% to 73%. The separation factors of PSG-J made with 80% toluene and 73% toluene were 2.55 and 2.51, respectively.

The resolution of naphthalene and pyrene differed significantly when comparing PSG monoliths made with 80% and 73% toluene. When the pore size decreased, which was brought about by using lower volumes of toluene, the PSG surface increased with a resulting increase in the retention and resolution under the same separation solution conditions. Thus, the permeability of the porous matrix affects the retention of the analytes.

While the invention has been described above by reference to various embodiments, it will be understood that changes and modifications may be made without departing from the scope of the invention. The present invention includes all that fits within the literal and equitable scope of the appended claims. All references referred to above are incorporated herein by reference in their entireties.

What is claimed is:

1. A method of preparing a porous matrix in a separation column, comprising:

providing a separation column;

providing an initial mixture of at least one porogen, at least one metal alkoxide, and at least one photoactive material selected from a group consisting of a photoactive group associated with the metal organic monomer, a photoinitiator, and any combination thereof, such that a resulting mixture that results from said initial mixture comprises a metal organic compound;

introducing the resulting mixture into the column; and irradiating the resulting mixture to form, via photoinitiated polymerization, a fritless, porous matrix comprising a metal organic polymer in the column.

2. The method of claim 1, wherein the matrix contains no chromatographic particles.

3. The method of claim 1, wherein the photoactive group is a methacrylate.

4. The method of claim 1, wherein the porogen is selected to controllably form pores in the matrix.

5. The method of claim 1, further comprising selecting a molar ratio of monomer to porogen to form pores in the matrix.

6. The method of claim 1, wherein the irradiating comprises irradiating the mixture with visible or ultraviolet light.

7. The method of claim 1, further comprising, after the irradiating, introducing an organic solvent into the column.

8. The method of claim 1, wherein the providing comprises providing a capillary or a planar structure.

* * * * *

UNITED STATES PATENT AND TRADEMARK OFFICE
CERTIFICATE OF CORRECTION

PATENT NO.       : 6,866,785 B2
APPLICATION NO. : 09/929275
DATED            : March 15, 2005
INVENTOR(S)      : Richard N. Zare et al.

It is certified that error appears in the above-identified patent and that said Letters Patent is hereby corrected as shown below:

Column 6, line 35, please delete "The fixture" and insert --The mixture--.

Column 6, line 46, please delete "maybe" and insert --may be--.

Column 6, line 67, please delete "is".

Column 7, line 14, please delete "includes" and insert --include--.

Column 8, line 27, please delete "matrix a" and insert --matrix, a--.

Column 9, line 21, please delete "usefull" and insert --useful--.

Column 9, line 32, please delete "Methacryloxypropyltrimetoxysilane" and insert --Methacryloxypropyltrimethoxysilane--.

Column 10, line 4, please delete "moniophasic" and insert --monophasic--.

Column 10, line 21, please delete "bonds" and insert --bond--.

Column 10, line 26, please delete "removed" and insert --remove--.

Column 10, line 39, please delete "band-held" and insert --hand-held--.

Column 10, line 51, please delete "(v/v)" and insert --(v/v/v)--.

Column 10, line 65, please delete "bienzanthracene" and insert --dibenzanthracene--.

Column 11, line 5, please delete "20° C." and insert --20° C--.

Column 11, line 7, please delete "ethylene/benzene" and insert --ethyl/benzene--.

Column 11, line 28, please delete "20° C." and insert --20° C--.

Column 12, line 18, please delete "X1-1500" and insert --XL-1500--.

Column 12, line 50, please delete "12.5. $\mu$M" and insert --12.5 $\mu$M--.

Column 12, line 63, please delete "heptanophenone;" and insert --heptanophenone,"

Column 13, line 15, please delete "poroux" and insert --porous--.

UNITED STATES PATENT AND TRADEMARK OFFICE
CERTIFICATE OF CORRECTION

PATENT NO.       : 6,866,785 B2
APPLICATION NO.  : 09/929275
DATED            : March 15, 2005
INVENTOR(S)      : Richard N. Zare et al.

It is certified that error appears in the above-identified patent and that said Letters Patent is hereby corrected as shown below:

Column 13, line 41, please delete "electropherogram" and insert --electrochromatogram--.

Column 13, line 53, please delete "The peak" and insert --The corrected peak--.

Column 13, line 55, please delete "arbitrary units/min".

Column 13, line 67, please fully justify the margin.

Column 14, line 25, please delete "angiotensis" and insert --angiotensin--.

Column 15, line 9, please delete "peak (3)" and insert --(peak 3)--.

Column 15, line 21, please delete "experimentation" and insert --experimental--.

Column 16, line 11, please delete "column" and insert --column.--.

Column 16, line 18, please delete "2.74-cm" and insert --2.74 cm--.

Column 16, line 26, please delete "kvalues" and insert --k values--.

Column 17, line 18, please delete "broadering" and insert --broadening--.

Column 19, line 46, please delete "5 kV" and insert --5kV--.

Column 20, line 63, please delete "$k=(t_R-t_o)/t_o$" and insert --$k=(t_R-t_0)/t_0$--.

Column 20, line 64, please delete "$t_o$" and inset --$t_0$--.

Column 21, line 3, in Table 3, please delete "$k_n$" and insert --$k_N$--.

Column 21, line 46, please delete "(Rs=2.43)" and insert --($R_s$=2.43)--.

Column 21, line 54, please delete "$k_N$ and $K_{Py}$" and insert --$k_N$ and $K_{Py}$--.

Column 21, line 58, please delete "$k_N$" and insert --$k_N$--.

Column 21, line 58, please delete "$k_{Py}$" and insert --$k_{Py}$--.

UNITED STATES PATENT AND TRADEMARK OFFICE
CERTIFICATE OF CORRECTION

PATENT NO. : 6,866,785 B2
APPLICATION NO. : 09/929275
DATED : March 15, 2005
INVENTOR(S) : Richard N. Zare et al.

It is certified that error appears in the above-identified patent and that said Letters Patent is hereby corrected as shown below:

Column 22, line 3, please delete "$k_N$" and insert --$k_N$--.

Column 22, line 4, please delete "$k_{Py}$" and insert --$k_{Py}$--.

Column 22, line 4, please delete "$k_N$" and insert --$k_N$--.

Column 22, line 4, please delete "$K_{Py}$" and insert --$k_{Py}$--.

Column 22, line 11, please delete "$k_N$" and insert --$k_N$--.

Column 22, line 12, please delete "$k_{Py}$" and insert --$k_{Py}$--.

Column 22, line 13, please delete "$k_N$" and insert --$k_N$--.

Column 22, line 13, please delete "$k_{Py}$" and insert --$k_{Py}$--.

Signed and Sealed this

Fifth Day of August, 2008

JON W. DUDAS
*Director of the United States Patent and Trademark Office*